US012758516B2

(12) United States Patent
Figarola et al.

(10) Patent No.: US 12,758,516 B2
(45) Date of Patent: Oct. 13, 2026

(54) COMPOUNDS FOR THE TREATMENT OF NEUROPATHIC PAIN

(71) Applicant: City of Hope, Duarte, CA (US)

(72) Inventors: James L. Figarola, Duarte, CA (US); Jyotirmoy Kusari, Duarte, CA (US); Arthur Riggs, Duarte, CA (US); David Horne, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 1127 days.

(21) Appl. No.: 17/439,933

(22) PCT Filed: Mar. 17, 2020

(86) PCT No.: PCT/US2020/023224
§ 371 (c)(1),
(2) Date: Sep. 16, 2021

(87) PCT Pub. No.: WO2020/190984
PCT Pub. Date: Sep. 24, 2020

(65) Prior Publication Data

US 2023/0048576 A1 Feb. 16, 2023

Related U.S. Application Data

(60) Provisional application No. 62/820,707, filed on Mar. 19, 2019.

(51) Int. Cl.

| | |
|---|---|
| ***A61K 31/192*** | (2006.01) |
| ***A61K 9/00*** | (2006.01) |
| ***A61K 31/196*** | (2006.01) |
| ***A61K 31/337*** | (2006.01) |
| ***A61K 31/573*** | (2006.01) |
| ***A61K 31/704*** | (2006.01) |
| ***A61K 33/243*** | (2019.01) |
| ***A61P 25/04*** | (2006.01) |

(52) U.S. Cl.
CPC .......... *A61K 31/192* (2013.01); *A61K 9/0019* (2013.01); *A61K 9/0056* (2013.01); *A61K 31/196* (2013.01); *A61K 31/337* (2013.01); *A61K 31/573* (2013.01); *A61K 31/704* (2013.01); *A61K 33/243* (2019.01); *A61P 25/04* (2018.01)

(58) Field of Classification Search
CPC ..... A61K 31/192; A61K 31/196; A61P 25/02; A61P 25/04
See application file for complete search history.

(56) References Cited

U.S. PATENT DOCUMENTS

2005/0171150 A1 8/2005 Rahbar et al.
2006/0264489 A1 11/2006 Palani et al.
2009/0030081 A1 1/2009 Rahbar et al.
2010/0112039 A1 5/2010 Estok et al.
2013/0253020 A1 9/2013 Tang et al.

FOREIGN PATENT DOCUMENTS

WO WO-2013/153092 A1 10/2013
WO WO-2019/094613 A1 5/2019

OTHER PUBLICATIONS

Figarola et al., "LR-90 a new advanced glycation endproduct inhibitor prevents progression of diabetic nephropathy in streptozotocin-diabetic rats", 2003, Diabetologia, 46, pp. 1140-1152 (Year: 2003).*
Figarola et al., "Anti-Inflammatory Effects of the Advanced Glycation End Product Inhibitor LR-90 in Human Monocytes", 2007, Diabetes, 56 pp. 647-655 (Year: 2007).*
Sekiguchi et al., "Paclitaxel-induced HMGB1 release from macrophages and its implication for peripheral neuropathy in mice: Evidence for a neuroimmune crosstalk", 2018, Neuropharmacology, 141, pp. 201-213 (Year: 2018).*
Wei et al., "Activation of RAGE/STAT3 pathway by methylglyoxal contributes to spinal central sensitization and persistent pain induced by bortezomib", 2017, Experimental Neurology, 296, pp. 74-82 (Year: 2017).*
Florence et al., "The Solubility of Drugs" In: Physicochemical Principles of Pharmacy, 1998, Palgrave, London, third edition, pp. 152-198 (Year: 1998).*
Gould et al., "2-Hydroxypropyl-B-cyclodextrin (HP-β-CD): A toxicology review", 2005, Food and Chemical Toxicology, 43, pp. 1451-1459 (Year: 2005).*
Nishida et al., "Involvement of high mobility group box 1 in the development and maintenance of chemotherapy-induced peripheral neuropathy in rats", 2016, Toxicology, 365, pp. 48-58 (Year: 2016).*
Gabrielsson et al., "In vivo potency revisited—Keep the target in sight", 2018, Pharmacology and Therapeutics, 184, pp. 177-188 (Year: 2018).*
Bowman, K.J. et al. (Jan. 5, 2001). "Differential effects of the poly (ADP-ribose) polymerase (PARP) inhibitor NU1025 on topoisomerase I and II inhibitor cytotoxicity in L1210 cells in vitro," *Br J Cancer* 84(1):106-112.
Boyette-Davis, J.A. et al. (Sep. 2011, e-published Jun. 24, 2011). "Follow-up psychophysical studies in bortezomib-related chemoneuropathy patients," *J Pain* 12(9):1017-1024.
Coffeen, U. et al. (May 3, 2019). "Chemotherapy-induced neuropathic pain characteristics in Mexico's National Cancer Center pain clinic," *J Pain Res* 12:1331-1339.
Dougherty, P.M. et al. (May 2004). "Taxol-induced sensory disturbance is characterized by preferential impairment of myelinated fiber function in cancer patients," *Pain* 109(1-2):132-142.
Hershman, D.L. et al. (Jun. 20, 2014, e-published Apr. 14, 2014). "Prevention and management of chemotherapy-induced peripheral neuropathy in survivors of adult cancers: American Society of Clinical Oncology clinical practice guideline," *J Clin Oncol* 32(18):1941-1967.
International Search Report mailed on Jun. 15, 2020 for PCT Application No. PCT/US2020/023224, filed Mar. 17, 2020, 3 pages.

(Continued)

*Primary Examiner* — Brenda L Coleman
*Assistant Examiner* — Madeline E Braun
(74) *Attorney, Agent, or Firm* — Mintz, Levin, Cohn, Ferris, Glovsky and Popeo, P.C.

(57) ABSTRACT

Provided herein are compositions including methylene bis [4,4'-(2-chlorophenylureidophenoxyisobutyric acid)] (LR-90) or a pharmaceutically acceptable salt or derivative thereof and methods of use thereof for treating and/or preventing chemotherapy-induced neuropathic pain in a subject in need thereof.

15 Claims, 6 Drawing Sheets

(56) References Cited

OTHER PUBLICATIONS

Mahtani, R.L. et al. (Feb. 8, 2018). "Comparative effectiveness of early-line nab-paclitaxel vs. paclitaxel in patients with metastatic breast cancer: a US community-based real-world analysis," *Cancer Manag Res* 10:249-256.
Muankaew, C. et al. (Jan. 2018, e-published Nov. 20, 2017). "Cyclodextrin-Based Formulations: A Non-Invasive Platform for Targeted Drug Delivery," *Basic Clin Pharmacol Toxicol* 122(1):46-55.
Nishida, T. et al. (Jul. 15, 2016, e-published Jul. 27, 2016). "Involvement of high mobility group box 1 in the development and maintenance of chemotherapy-induced peripheral neuropathy in rats," *Toxicology* 365:48-68.
Pacher, P. et al. (Mar. 2002). "Activation of poly(ADP-ribose) polymerase contributes to development of doxorubicin-induced heart failure," *J Pharmacol Exp Ther* 300(3):862-867.
Soriano, F.G. et al. (Oct. 12, 2001). "Rapid reversal of the diabetic endothelial dysfunction by pharmacological inhibition of poly(ADP-ribose) polymerase," *Circ Res* 89(8):684-691.
Van Den Bent, M.J. et al. (Jun. 1997). "Progression of paclitaxel-induced neuropathy following discontinuation of treatment," *Muscle Nerve* 20(6):750-752.
Written Opinion mailed on Jun. 15, 2020 for PCT Application No. PCT/US2020/023224, filed Mar. 17, 2020, 9 pages.

* cited by examiner

COMPOUNDS FOR THE TREATMENT OF NEUROPATHIC PAIN

CROSS-REFERENCE TO RELATED APPLICATION

This application is a U.S. National Stage Entry of the International Patent Application No. PCT/US2020/023224, filed on Mar. 17, 2020, which claims priority to U.S. Provisional Application No. 62/820,707, filed Mar. 19, 2019, the disclosure of which is incorporated herein in their entireties and for all purposes.

BACKGROUND

Neuropathic pain can occur as a result of damage to the peripheral or central nervous system. In many pain patients, in particular those with chronic pain conditions, pain is inadequately managed.

Chemotherapy-induced neuropathic pain (CINP) is a specific type of neuropathic pain, and is a serious complication associated with anticancer drugs. CINP may lead to a lower quality of life and dysfunction of the sensory, motor, and autonomic systems. CINP often causes patients to discontinue chemotherapy. Patients describe a range of sensory, bilateral symptoms in both hands and feet (also described as a stocking and glove distribution) including numbness, tingling, ongoing/spontaneous pain, and hypersensitivity to mechanical and/or cold stimuli. Pain and sensory abnormalities can persist for months or years following the cessation of chemotherapy. Therefore, patients may well be cancer-free, but suffering a debilitating painful neuropathy as a result of their cancer treatment.

BRIEF SUMMARY

In view of the foregoing, there is a need for compounds and methods to treat and prevent chemotherapy-induced neuropathic pain (CINP). The present disclosure addresses this need, and provides additional benefits as well.

In an aspect, provided herein are methods of treating chemotherapy-induced neuropathic pain in a subject in need thereof. The methods include administering to the subject an effective amount of methylene bis[4,4'-(2-chlorophenylureidophenoxyisobutyric acid)] (LR-90) or a pharmaceutically acceptable salt or derivative thereof.

In an aspect, provided herein are methods of preventing chemotherapy-induced neuropathic pain in a subject in need thereof. The methods include administering to the subject an effective amount of methylene bis[4,4'-(2-chlorophenylureidophenoxyisobutyric acid)] (LR-90) or a pharmaceutically acceptable salt or derivative thereof.

In an aspect, provided herein are compositions including a chemotherapeutic compound (e.g., a mitotic inhibitor) and methylene bis[4,4'-(2-chlorophenylureidophenoxyisobutyric acid)] (LR-90) or a pharmaceutically acceptable salt or derivative thereof.

In an aspect, provided herein are pharmaceutical compositions including (a) LR-90 or a pharmaceutically acceptable salt or derivative thereof, and (b) a pharmaceutically acceptable organic solvent.

In an aspect, provided herein are kits including a chemotherapeutic compound (e.g. a mitotic inhibitor) and methylene bis[4,4'-(2-chlorophenylureidophenoxyisobutyric acid)] (LR-90) or a pharmaceutically acceptable salt or derivative thereof.

In an aspect, provided herein are uses of methylene bis[4,4'-(2-chlorophenylureidophenoxyisobutyric acid)] (LR-90) or a pharmaceutically acceptable salt or derivative thereof in treating or preventing chemotherapy-induced neuropathic pain in a subject in need thereof.

DETAILED DESCRIPTION

Figure 1:
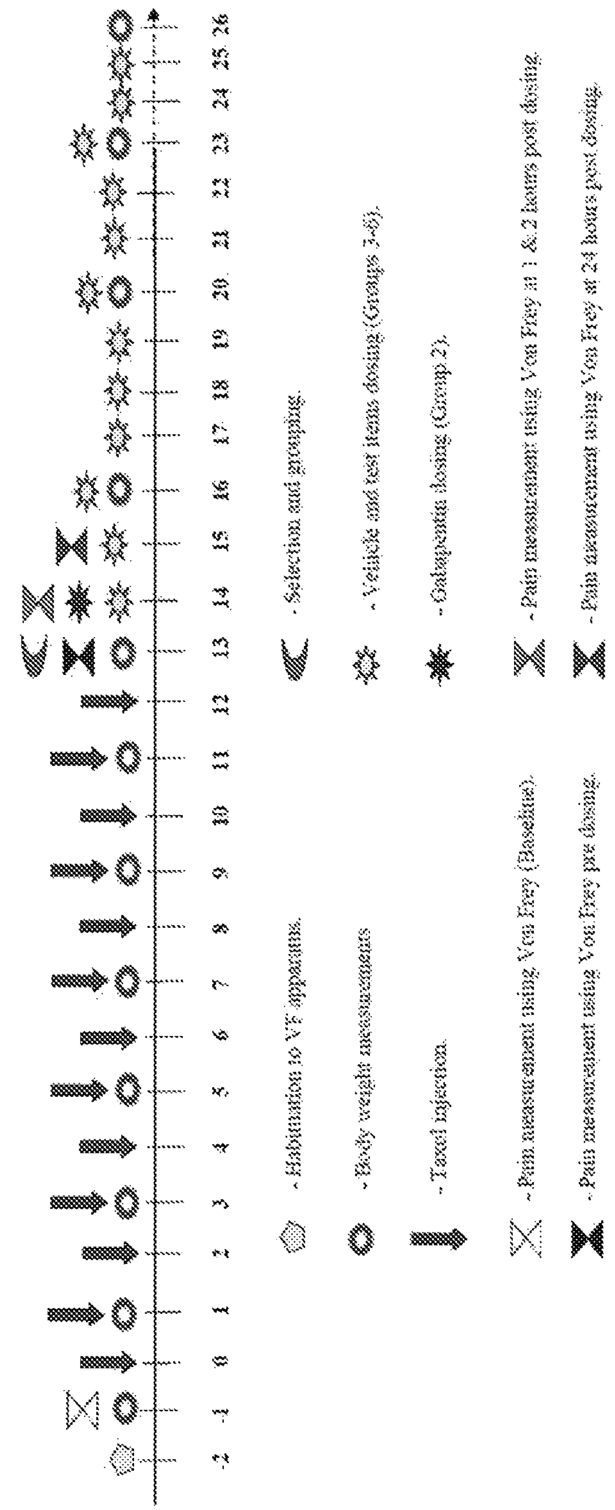
FIG. 1 is an example schematic illustration of taxol induction and treatment.

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. [See, for example, Refs. 5-12].

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art.

As used herein, the singular terms “a”, “an”, and “the” include the plural reference unless the context clearly indicates otherwise.

Reference throughout this specification to, for example, “one embodiment”, “an embodiment”, “another embodiment”, “a particular embodiment”, “a related embodiment”, “a certain embodiment”, “an additional embodiment”, or “a further embodiment” or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification; unless the context requires otherwise, the words "comprise", "comprises" and "comprising" will be understood to imply the inclusion of a stated step or element or group of steps or elements but pot the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including-any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

The terms "disease" or "condition" refer to a state of being or health status of a patient or subject capable of being diagnosed and/or treated with compounds or methods provided herein. The condition may be a neuropathic pain. The condition may be chemotherapy-induced neuropathic pain.

"Neuropathic pain" as used herein is a category of pain that includes several forms of chronic pain and which results from dysfunction of nervous rather than somatic tissue. Neuropathic pain, that is pain deriving from dysfunction of the central or peripheral nervous system, may also be a consequence of damage to peripheral nerves or to regions of the central nervous system, may result from disease, or may be idiopathic. Neuropathic pain includes, without limitation, peripheral neuropathic pain, central neuropathic pain, and mixed neuropathic pain. In embodiments, the neuropathic pain is neuropathic pain induced by treatment with a chemotherapeutic agent. In embodiments, the neuropathic pain is chemotherapy-induced neuropathic pain (CINP). CINP is often due to the toxicity of the chemotherapeutic drugs, and typically affects the peripheral nervous system (referred to as "chemotherapy-induced peripheral neuropathy"). The severity of the resultant neuropathy depends on the drugs used, duration of treatment, and/or nerve damage by cancer itself or due to any pre-existing conditions. CINP can manifest in several ways. It may affect small diameter nerve fibers causing burning pain, hyperesthesia, and later on loss of pain and temperature sensations. Effects on large diameter nerve fibers cause loss of vibration sense, proprioception, and slowing of nerve conduction. Common presentations include sensory disturbances such as numbness, pain, paraesthesia, hypoaesthesia, and dysaesthesia. Neuropathy may simultaneously affect upper and lower extremities and also the cranial nerves. Deep tendon reflexes, proprioception, vibration, two-point discrimination, and temperature sensation may be lost. For additional information relating to CINP, see, e.g., Dougherty et al., [1]; van den Bent et al [2], Boyette-Davis et al. [3]; and Hershman et al. [4].

"Treating" or "treatment" as used herein broadly includes any approach for obtaining beneficial or desired results in a subject's condition, including clinical results. Beneficial or desired clinical results can include, but are not limited to, alleviation or amelioration of one or more symptoms or conditions, diminishment of the extent of a condition, stabilizing (i.e., not worsening) the state of disease or condition, delay or slowing of disease progression, amelioration or palliation of the disease state, diminishment of the reoccurrence of disease, and remission, whether partial or total and whether detectable or undetectable. In other words, "treatment" as used herein includes any cure or amelioration of a disease. Treatment may relieve the disease's symptoms fully or partially remove the disease's underlying cause, shorten a disease's duration, or do a combination of these things. In the case of chemotherapy-induced neuropathic pain, treatment may include slowing or halting worsening of pain in a subject, or reducing or eliminating pain experienced by a subject following chemotherapy treatment. In embodiments, the duration or severity of neuropathic pain is reduced by at least about 5%, 10%, 20%, 30%, 40%, 50%, 60%, 70%, or more. In embodiments, duration or severity is reduced by at least about 25%.

"Preventing" as used herein refers to a decrease in the occurrence or incidence of one or more disease symptoms in a patient. Prevention may be complete (no detectable symptoms) or partial, such that fewer symptoms are observed than would likely occur absent treatment. Prevention includes prophylactic treatment. In the case of chemotherapy-induced neuropathic pain, prevention may include administering a composition of the present disclosure to a subject prior to chemotherapy, concurrently with chemotherapy, or prior to experiencing chemotherapy-induced neuropathic pain, with the result that experience of neuropathic pain following chemotherapy is avoided, has a reduced incidence, has a delayed onset, has a reduced severity, or a combination of these, relative to what would likely occur absent treatment to prevent such pain. In embodiments, the incidence, onset, and/or severity of neuropathic pain is reduced by at least about 5%, 10%, 20%, 30%, 40%, 50%, 60%, 70%, or more. In embodiments, the incidence, onset, and/or severity of neuropathic pain is reduced by at least about 25%.

The term "patient" or "subject" refers to a living organism suffering from or prone to a disease or condition that can be treated by administration of a pharmaceutical composition. Non-limiting examples include humans, other mammals, bovines, rats, mice, dogs, monkeys, goat, sheep, cows, deer, and other non-mammalian animals. In some embodiments, a subject is human.

An "effective amount" is an amount sufficient for a compound to accomplish a stated purpose relative to the absence of the compound (e.g. achieve the effect for which it is administered, treat a disease or condition, prevent a disease or condition, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques.

The term "administering" as used herein includes, without limitation, oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

The term "co-administer" as used herein refers to a composition described herein administered at the same time, just prior to, or just after the administration of one or more additional therapies. The compounds provided herein can be administered alone or can be co-administered to the patient. Co-administration is meant to include simultaneous or sequential administration of the compounds individually or in combination (more than one compound). Thus, the preparations can also be combined, when desired, with other active substances (e.g. to reduce metabolic degradation).

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, [13]). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an a vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

Methods

In an aspect, provided herein are methods of treating chemotherapy-induced neuropathic pain in a subject in need thereof. The methods include administering to the subject an effective amount of methylene bis[4,4'-(2-chlorophenylureidophenoxyisobutyric acid)] (LR-90) or a pharmaceutically acceptable salt or derivative thereof. In embodiments, the LR-90 or pharmaceutically acceptable salt or derivative thereof is part of a composition (e.g., a pharmaceutical composition) as described herein. In embodiments, the pharmaceutical composition includes a pharmaceutically acceptable carrier, such as an organic solvent, in accordance with any of the various compositions described herein.

In an aspect, provided herein are methods of preventing chemotherapy-induced neuropathic pain in a subject in need thereof. The methods include administering to the subject an effective amount of methylene bis[4,4'-(2-chlorophenylureidophenoxyisobutyric acid)] (LR-90) or a pharmaceutically acceptable salt or derivative thereof. In embodiments, the LR-90 or pharmaceutically acceptable salt or derivative thereof is part of a composition (e.g., a pharmaceutical composition) as described herein. In embodiments, the pharmaceutical composition includes a pharmaceutically acceptable carrier, such as an organic solvent, in accordance with any of the various compositions described herein.

In embodiments, the subject has cancer. In embodiments, the cancer is a solid tumor cancer. In embodiments, the cancer is prostate cancer, hormone-refractory prostate cancer, ovarian cancer, breast cancer, head and neck cancer, stomach cancer, lung cancer, non-small cell lung cancer, Kaposi sarcoma, cervical cancer, pancreatic cancer, melanoma, or esophageal cancer. In embodiments, the cancer is prostate cancer. In embodiments, the cancer is hormone-refractory prostate cancer. In embodiments, the cancer is ovarian cancer. In embodiments, the cancer is breast cancer. In embodiments, the cancer is head and neck cancer. In embodiments, the cancer is stomach cancer. In embodiments, the cancer is lung cancer. In embodiments, the cancer is non-small cell lung cancer. In embodiments, the cancer is Kaposi sarcoma. In embodiments, the cancer is cervical cancer. In embodiments, the cancer is pancreatic cancer. In embodiments, the cancer is melanoma. In embodiments, the cancer is esophageal cancer.

In embodiments, the subject is receiving or has been prescribed treatment with one or more anti-cancer agents. In general, an anti-cancer agent refers to an agent having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126; PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid, ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor, bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine;

edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor, leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor, mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor, multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer, ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator, protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone Bi; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofluran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor, stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor, translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer, carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, Inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), immunotherapy (e.g., cellular immunotherapy, antibody therapy, cytokine therapy, combination immunotherapy, etc.), radioimmunotherapy (e.g., anti-CD20 monoclonal antibody conjugated to $^{111}In$, $^{90}Y$, or $^{131}I$, etc.), immune checkpoint inhibitors (e.g., CTLA4 blockade, PD-1 inhibitors, PD-L1 inhibitors, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

The chemotherapeutic agents commonly associated with CINP are platinum compounds (cisplatin, carboplatin, and oxaliplatin), taxanes (paclitaxel, docetaxel), *vinca* alkaloids (vincristine, vinblastine), epothilones (ixabepilone), bortezomib, and thalidomide along with its analogues. Combination of two or more of these agents can result in higher possibility of developing CINP.

In embodiments, the subject is receiving or has been prescribed treatment with one or more chemotherapeutic compounds. In embodiments, the chemotherapeutic compound is selected from platinum compounds, cytotoxic antibiotics, antimetabolites, anti-mitotic agents, alkylating agents, arsenic compounds, DNA topoisomerase inhibitors, taxanes, nucleoside analogues, plant alkaloids, and toxins; and synthetic derivatives thereof. In embodiments, the chemotherapeutic compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In embodiments, PARP (e.g., PARP-1 and/or PARP-2) inhibitors are used and such inhibitors are known (e.g., Olaparib, ABT-888, BSI-201, BGP-15 (N-Gene Research Laboratories, Inc.); INO-1001 (Inotek Pharmaceuticals Inc.); PJ34 [See, for example, Refs. 14-15]; 3-aminobenzamide (Trevigen); 4-amino-1,8-naphthalimide; (Trevigen); 6(5H)-phenanthridinone (Trevigen); benzamide [See, for example, Ref. 16]; and NU1025 [See, for example, Ref. 17].

In embodiments, the subject is receiving or has been prescribed treatment with one or more chemotherapeutic compounds including a mitotic inhibitor. In embodiments, the mitotic inhibitor is vincristine, vinblastine, etoposide, teniposide, ixabepilone, nocodazole, epothilone, vinorelbine, camptothecin, irinotecan, topotecan, amsacrine, lamellarin D, or a taxane. In embodiments, the mitotic inhibitor is vincristine. In embodiments, the mitotic inhibitor is vinblastine. In embodiments, the mitotic inhibitor isetoposide. In embodiments, the mitotic inhibitor is teniposide. In embodiments, the mitotic inhibitor is ixabenpilone. In embodiments, the mitotic inhibitor is nocodazole. In embodiments, the mitotic inhibitor is epothilone. In embodiments, the mitotic inhibitor is vnorelbine. In embodiments, the mitotic inhibitor is camptothecin. In embodiments, the mitotic inhibitor is irinotecan. In embodiments, the mitotic inhibitor istopotecan. In embodiments, the mitotic inhibitor is amsacrine. In embodiments, the mitotic inhibitor is lamellarin D. In embodiments, the mitotic inhibitor is a taxane. In embodiments, the taxane is cabazitaxel, paclitaxel, 10-deacetylbaccatin III, baccatin III, paclitaxel C, 7-epipaclitaxel, or docetaxel. In embodiments, the taxane is albumin-bound paclitaxel.

In embodiments, the subject is receiving or has been prescribed treatment with cisplatin, dexamethasone, doxorubicin, etoposide, bortezomib, or vinblastine. In embodiments, the subject is receiving or has been prescribed treatment with cisplatin. In embodiments, the subject is receiving or has been prescribed treatment with dexamethasone. In embodiments, the subject is receiving or has been prescribed treatment with doxorubicin. In embodiments, the subject is receiving or has been prescribed treatment with etoposide. In embodiments, the subject is receiving or has been prescribed treatment with bortezomib. In embodiments, the subject is receiving or has been prescribed treatment with vinblastine.

In embodiments, methods provided herein for treating chemotherapy-induced neuropathic pain in a subject include administering to the subject an effective amount of methylene bis[4,4'-(2-chlorophenylureidophenoxyisobutyric acid)] (LR-90) or a pharmaceutically acceptable salt or derivative thereof. In embodiments, an effective amount for treating chemotherapy-induced neuropathic pain is about 1 mg to about 200 mg, about 5 mg to about 175 mg, about 10 mg to about 150 mg, about 25 mg to about 125 mg, about 1 mg to about 100 mg, about 10 mg to about 90 mg, about 20 mg to about 80 mg, about 30 mg to about 70 mg, about 40 mg to about 60 mg, or about 50 mg of LR-90 per kilogram weight of subject. In embodiments, an effective amount for treating chemotherapy-induced neuropathic pain is about 1 to about 10 mg, about 2 to about 9 mg, about 3 mg to about 8 mg, about 4 mg to about 7 mg, or about 5 to about 6 mg of LR-90 per kilogram weight of subject. In embodiments, an effective amount of LR-90 is about or at most about 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, or more per kilogram weight of subject. In embodiments, the effective amount of LR-90 is about or at most about 20 mg. In embodiments, the effective amount of LR-90 is about or at most about 15 mg. In embodiments, the effective amount of LR-90 is about or at most about 14 mg. In embodiments, the effective amount of LR-90 is about or at most about 13 mg. In embodiments, the effective amount of LR-90 is about or at most about 12 mg. In embodiments, the effective amount of LR-90 is about or at most about 11 mg. In embodiments, the effective amount of LR-90 is about or at most about 10 mg. In embodiments, the effective amount of LR-90 is about or at most about 9 mg. In embodiments, the effective amount of LR-90 is about or at most about 8 mg. In embodiments, the effective amount of LR-90 is about or at most about 7 mg. In embodiments, the effective amount of LR-90 is about or at most about 6 mg. In embodiments, the effective amount of LR-90 is about or at most about 5 mg. In embodiments, an effective amount for treating chemotherapy-induced neuropathic pain is about 1 to about 100 mg of LR-90 per kilogram weight of subject. In embodiments, an effective amount for treating chemotherapy-induced neuropathic pain is about 50 to about 100 mg of LR-90 per kilogram weight of subject. In embodiments, the effective amount is about 1 to about 10 mg of LR-90 per kilogram weight of subject. In embodiments, dosing is calculated based on a subject weight of about 70 kg.

In embodiments, methods provided herein for preventing chemotherapy-induced neuropathic pain in a subject include administering to the subject an effective amount of methylene bis[4,4'-(2-chlorophenylureidophenoxyisobutyric acid)] (LR-90) or a pharmaceutically acceptable salt or derivative thereof. In embodiments, an effective amount for preventing chemotherapy-induced neuropathic pain is about 1 mg to about 200 mg, about 5 mg to about 175 mg, about 10 mg to about 150 mg, about 25 mg to about 125 mg, 1 mg to about 100 mg, about 10 mg to about 90 mg, about 20 mg to about 80 mg, about 30 mg to about 70 mg, about 40 mg to about 60 mg, or about 50 mg of LR-90 per kilogram weight of subject. In embodiments, an effective amount for preventing chemotherapy-induced neuropathic pain is about 1 to about 10 mg, about 2 to about 9 mg, about 3 mg to about 8 mg, about 4 mg to about 7 mg, or about 5 to about 6 mg of LR-90 per kilogram weight of subject. In embodiments, an effective amount of LR-90 is about or at most about 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, or more per kilogram weight of subject. In embodiments, the effective amount of LR-90 is about or at most about 20 mg. In embodiments, the effective amount of LR-90 is about or at most about 15 mg. In embodiments, the effective amount of LR-90 is about or at most about 14 mg. In embodiments, the effective amount of LR-90 is about or at most about 13 mg. In embodiments, the effective amount of LR-90 is about or at most about 12 mg. In embodiments, the effective amount of LR-90 is about or at most about 11 mg. In embodiments, the effective amount of LR-90 is about or at most about 10 mg. In embodiments, the effective amount of LR-90 is about or at most about 9 mg. In embodiments, the effective amount of LR-90 is about or at most about 8 mg. In embodiments, the effective amount of LR-90 is about or at most about 7 mg. In embodiments, the effective amount of LR-90 is about or at most about 6 mg. In embodiments, the effective amount of LR-90 is about or at most about 5 mg. In embodiments, an effective amount for preventing chemotherapy-induced neuropathic pain is about 1 to about 100 mg of LR-90 per kilogram weight of subject. In embodiments, an effective amount for preventing chemotherapy-induced neuropathic pain is about 50 to about 100 mg of LR-90 per kilogram weight of subject. In embodiments, an effective amount for preventing chemotherapy-induced neuropathic pain is about 1 to about 10 mg of LR-90 per kilogram weight of subject. In embodiments, dosing is calculated based on a subject weight of about 70 kg.

In embodiments, the effective amount of LR-90 is administered multiple times at regular or irregular intervals, such as one or more times per day or one or more times per week. In embodiments, the effective amount of LR-90 is administered 1, 2, 3, 4, or 5 times per day, or more. In embodiments, the effective amount is administered once per day. In embodiments, the effective amount is administered 2 times per day. In embodiments, the effective amount is administered 3 times per day. In embodiments, the effective amount is administered 4 times per day. In embodiments, the effective amount is administered 5 times per day. In embodiments, the effective amount of LR-90 is administered 1, 2, 3, 4, 5, 6, or 7 times per week, or more. In embodiments, the effective amount is administered once per week. In embodiments, the effective amount is administered 2 times per week. In embodiments, the effective amount is administered 3 times per week. In embodiments, the effective amount is administered 4 times per week. In embodiments, the effective amount is administered 5 times per week. In embodiments, the effective amount is administered 6 times per week. In embodiments, the effective amount is administered 7 times per week. The effective amount of LR-90 can be any of the amounts described herein. In embodiments, the effective amount is the amount administered at each of multiple administrations (e.g., each daily or weekly dose, or each of two or more doses in a day or week). In embodiments, the effective amount of LR-90 is a dose of about 50 mg to about 100 mg of LR-90 per kilogram weight of subject, and the dose is administered two or more times per day. In embodiments, dosing is calculated based on a subject weight of about 70 kg.

In embodiments, the effective amount of LR-90 is a dose of about 1 mg to about 200 mg per kilogram weight of subject, and the dose is administered two or more times per day. In embodiments, the effective amount of LR-90 is a dose of about 5 mg to about 175 mg per kilogram weight of subject, and the dose is administered two or more times per day. In embodiments, the effective amount of LR-90 is a dose of about 10 mg to about 150 mg per kilogram weight of subject, and the dose is administered two or more times per day. In embodiments, the effective amount of LR-90 is a dose of about 25 mg to about 125 mg per kilogram weight of subject, and the dose is administered two or more times per day. In embodiments, the effective amount of LR-90 is a dose of about 1 mg to about 100 mg per kilogram weight of subject, and the dose is administered two or more times per day. In embodiments, the effective amount of LR-90 is a dose of about 10 mg to about 90 mg per kilogram weight of subject, and the dose is administered two or more times per day. In embodiments, the effective amount of LR-90 is a dose of about 20 mg to about 80 mg per kilogram weight of subject, and the dose is administered two or more times per day. In embodiments, the effective amount of LR-90 is a dose of about 30 mg to about 70 mg per kilogram weight of subject, and the dose is administered two or more times per day. In embodiments, the effective amount of LR-90 is a dose of about 50 mg per kilogram weight of subject, and the dose is administered two or more times per day. In embodiments, dosing is calculated based on a subject weight of about 70 kg.

In embodiments, the effective amount of LR-90 is a dose of about or at least about 1 mg per kilogram weight of subject, and the dose is administered two or more times per day. In embodiments, the effective amount of LR-90 is a dose of about or at least about 5 mg per kilogram weight of subject, and the dose is administered two or more times per day. In embodiments, the effective amount of LR-90 is a dose of about or at least about 10 mg per kilogram weight of subject, and the dose is administered two or more times per day. In embodiments, the effective amount of LR-90 is a dose of about or at least about 25 mg per kilogram weight of subject, and the dose is administered two or more times per day. In embodiments, the effective amount of LR-90 is a dose of about or at least about 20 mg per kilogram weight of subject, and the dose is administered two or more times per day. In embodiments, the effective amount of LR-90 is a dose of about or at least about 30 mg per kilogram weight of subject, and the dose is administered two or more times per day. In embodiments, the effective amount of LR-90 is a dose of about or more than about 50 mg per kilogram weight of subject, and the dose is administered two or more times per day. In embodiments, the effective amount of LR-90 is a dose of about or less than about 200 mg per kilogram weight of subject, and the dose is administered two or more times per day. In embodiments, the effective amount of LR-90 is a dose of about or less than about 175 mg per kilogram weight of subject, and the dose is administered two or more times per day. In embodiments, the effective amount of LR-90 is a dose of about or less than about 150 mg per kilogram weight of subject, and the dose is administered two or more times per day. In embodiments, the effective amount of LR-90 is a dose of about or less than about 125 mg per kilogram weight of subject, and the dose is administered two or more times per day. In embodiments, the effective amount of LR-90 is a dose of about or less than about 100 mg per kilogram weight of subject, and the dose is administered two or more times per day. In embodiments, the effective amount of LR-90 is a dose of about or less than about 90 mg per kilogram weight of subject, and the dose is administered two or more times per day. In embodiments, the effective amount of LR-90 is a dose of about or less than about 80 mg per kilogram weight of subject, and the dose is administered two or more times per day. In embodiments, the effective amount of LR-90 is a dose of about or less than about 70 mg per kilogram weight of subject, and the dose is administered two or more times per day. In embodiments, the effective amount of LR-90 is a dose of about or less than about 50 mg per kilogram weight of subject, and the dose is administered two or more times per day. In embodiments, dosing is calculated based on a subject weight of about 70 kg.

In embodiments, LR-90 is administered before, together with, concurrently with, or after a chemotherapeutic compound. In embodiments, LR-90 is administered before a chemotherapeutic compound. In embodiments, LR-90 is administered together with a chemotherapeutic compound. In embodiments, LR-90 is administered concurrently with a chemotherapeutic compound. In embodiments, LR-90 is administered after a chemotherapeutic compound. In embodiments, the chemotherapeutic compound administered may be any one of the chemotherapeutic agents described above.

In embodiments, the methods provided herein include administering LR-90 via administration routes including nasal, oral, parenteral, intramuscular, intra-articular, intravenous, subcutaneous, transdermal, ocular and aural administration. In embodiments, the methods provided herein include administering LR-90 via nasal administration. In embodiments, the methods provided herein include administering LR-90 via oral administration. In embodiments, the methods provided herein include administering LR-90 via parenteral administration. In embodiments, the methods provided herein include administering LR-90 via intramuscular administration. In embodiments, the methods provided herein include administering LR-90 via intra-articular administration. In embodiments, the methods provided herein include administering LR-90 via intravenous administration. In embodiments, the methods provided herein include administering LR-90 via subcutaneous administration. In embodiments, the methods provided herein include administering LR-90 via transdermal administration. In embodiments, the methods provided herein include administering LR-90 via ocular administration. In embodiments, the methods provided herein include administering LR-90 via aural administration.

In embodiments, the methods provided herein include administering the chemotherapeutic compound via nasal, oral, parenteral, intramuscular, intra-articular, intravenous, subcutaneous, transdermal, ocular or aural administration. In embodiments, the methods provided herein include administering chemotherapeutic compound via nasal administration. In embodiments, the methods provided herein include administering chemotherapeutic compound via oral administration. In embodiments, the methods provided herein include administering chemotherapeutic compound via parenteral administration. In embodiments, the methods provided herein include administering chemotherapeutic compound via intramuscular administration. In embodiments, the methods provided herein include administering chemotherapeutic compound via intra-articular administration. In embodiments, the methods provided herein include administering chemotherapeutic compound via intravenous administration. In embodiments, the methods provided herein include administering chemotherapeutic compound via subcutaneous administration. In embodiments, the methods provided herein include administering chemotherapeutic compound via transdermal administration. In embodiments, the methods provided herein include administering chemotherapeutic compound via ocular administration. In embodiments, the methods provided herein include administering chemotherapeutic compound via aural administration.

In embodiments, LR-90 is administered concurrently or separately from a chemotherapeutic agent. Administration of LR-90 and the chemotherapeutic agent can be by the same route or by different routes. Administration by the same route includes, but is not limited to, administration as a single composition, administration as separate compositions at the same location, and administration as separate compositions at different locations but still by the same route (e.g., intravenous injection into different veins). Administration by different routes include any of the routes described above, in any combination. Non-limiting examples of administration routes include oral, rectal, sublingual, topical, nasal, transdermal, and parenteral routes. In embodiments, LR-90 is administered via oral administration (referred to as orally) and the chemotherapeutic compound is administered via intravenous administration (referred to as intravenously).

In an aspect, provided herein are uses of LR-90 or a pharmaceutically acceptable salt or derivative thereof in treating or preventing chemotherapy-induced neuropathic pain in a subject in need thereof. In embodiments, treating chemotherapy-induced neuropathic pain includes slowing or halting worsening of pain in a subject, or reducing or eliminating pain experienced by a subject following chemotherapy treatment. In embodiments, treating chemotherapy-induced neuropathic pain includes slowing or halting worsening and/or reducing or eliminating numbness, pain, paraesthesia, hypoaesthesia, dysaesthesia, and/or loss of deep tendon reflexes, proprioception, vibration, two-point discrimination, and/or temperature sensation or a combination thereof. In embodiments, treating chemotherapy-induced neuropathic pain includes slowing or halting worsening and/or reducing or eliminating numbness. In embodiments, treating chemotherapy-induced neuropathic pain includes slowing or halting worsening and/or reducing or eliminating pain. In embodiments, treating chemotherapy-induced neuropathic pain includes slowing or halting worsening and/or reducing or eliminating paraesthesia. In embodiments, treating chemotherapy-induced neuropathic pain includes slowing or halting worsening and/or reducing or eliminating hypoaesthesia. In embodiments, treating chemotherapy-induced neuropathic pain includes slowing or halting worsening and/or reducing or eliminating dysaesthesia. In embodiments, treating chemotherapy-induced neuropathic pain includes slowing or halting worsening and/or reducing or eliminating loss of deep tendon reflexes. In embodiments, treating chemotherapy-induced neuropathic pain includes slowing or halting worsening and/or reducing or eliminating loss of proprioception. In embodiments, treating-chemotherapy-induced neuropathic pain includes slowing or halting worsening and/or reducing or eliminating loss of vibration. In embodiments, treating chemotherapy-induced neuropathic pain includes slowing or halting worsening and/or reducing or eliminating loss of two-point discrimination. In embodiments, treating chemotherapy-induced neuropathic pain includes slowing or halting worsening and/or reducing or eliminating loss of temperature sensation.

In embodiments, preventing chemotherapy-induced neuropathic pain includes a decrease in the occurrence or incidence of one or more disease symptoms in a patient. In embodiments, preventing chemotherapy-induced neuropathic pain includes a decrease in the occurrence or incidence of numbness, pain, paraesthesia, hypoaesthesia, dysaesthesia, loss of deep tendon reflexes, proprioception, vibration, two-point discrimination, and/or temperature sensation or a combination thereof. In embodiments, preventing chemotherapy-induced neuropathic pain includes a decrease in the occurrence or incidence of numbness. In embodiments, preventing chemotherapy-induced neuropathic pain includes a decrease in the occurrence or incidence of pain. In embodiments, preventing chemotherapy-induced neuropathic pain includes a decrease in the occurrence or incidence of paraesthesia. In embodiments, preventing chemotherapy-induced neuropathic pain includes a decrease in the occurrence or incidence of hypoaesthesia. In embodiments, preventing chemotherapy-induced neuropathic pain includes a decrease in the occurrence or incidence of dysaesthesia. In embodiments, preventing chemotherapy-induced neuropathic pain includes a decrease in the occurrence or incidence of loss of deep tendon reflexes. In embodiments, preventing chemotherapy-induced neuropathic pain includes a decrease in the occurrence or incidence of loss of proprioception. In embodiments, preventing chemotherapy-induced neuropathic pain includes a decrease in the occurrence or incidence of loss of vibration. In embodiments, preventing chemotherapy-induced neuropathic pain includes a decrease in the occurrence or incidence of loss of two-point discrimination. In embodiments, preventing chemotherapy-induced neuropathic pain includes a decrease in the occurrence or incidence of loss of temperature sensation.

Compositions

In an aspect, provided herein are compositions comprising a chemotherapeutic compound and LR-90 or a pharmaceutically acceptable salt or derivative thereof. The chemotherapeutic compound can be any chemotherapeutic compound described herein, including examples described in connection with the various methods of the present disclosure. In embodiments, the chemotherapeutic agent is a mitotic inhibitor. The mitotic inhibitor can be any mitotic inhibitor described herein, including examples described in connection with the various methods of the present disclosure. In embodiments, the LR-90 or pharmaceutically acceptable salt or derivative thereof is part of a pharmaceutical composition as described herein. In embodiments, the pharmaceutical composition includes a pharmaceutically acceptable carrier, such as an organic solvent, in accordance with any of the various compositions described herein.

In an aspect, provided herein are pharmaceutical compositions including (a) LR-90 or a pharmaceutically acceptable salt or derivative thereof, and (b) a pharmaceutically acceptable organic solvent. In embodiments, the pharmaceutical formulation further includes a chemotherapeutic compound, such as a mitotic inhibitor.

A variety of mitotic inhibitors are available. In embodiments, the mitotic inhibitor is vincristine, vinblastine, etoposide, teniposide, ixabepilone, nocodazole, epothilone, vinorelbine, camptothecin, irinotecan, topotecan, amsacrine, lamellarin D, or a taxane. In embodiments, the mitotic inhibitor is vincristine. In embodiments, the mitotic inhibitor is vinblastine. In embodiments, the mitotic inhibitor isetoposide. In embodiments, the mitotic inhibitor is teniposide. In embodiments, the mitotic inhibitor is ixabenpilone. In embodiments, the mitotic inhibitor is nocodazole. In embodiments, the mitotic inhibitor is epothilone. In embodiments, the mitotic inhibitor is vnorelbine. In embodiments, the mitotic inhibitor is camptothecin. In embodiments, the mitotic inhibitor is irinotecan. In embodiments, the mitotic inhibitor istopotecan. In embodiments, the mitotic inhibitor is amsacrine. In embodiments, the mitotic inhibitor is lamellarin D. In embodiments, the mitotic inhibitor is taxane. In embodiments, the taxane is cabazitaxel, paclitaxel, 10-deacetylbaccatin III, baccatin III, paclitaxel C, 7-epipaclitaxel, or docetaxel. In embodiments, the taxane is albumin-bound paclitaxel.

"LR90" as used herein refers to methylene bis[4,4'-(2-chlorophenylureidophenoxyisobutyric acid)]arylureidophenoxyisobutyric acids and has the structure depicted below:

LR90

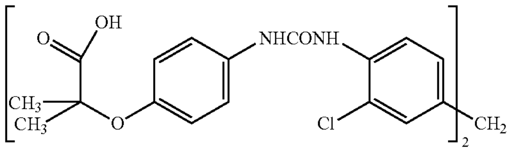

Accordingly, the compounds referred to herein, their pharmaceutically acceptable salts and derivatives, and compositions comprising such compounds, salts, and derivatives can be useful in providing benefits to those suffering from or at risk of developing chemotherapy-induced neuropathic pain.

Dosages and effective amounts for administration of the compounds and compositions in the methods described herein can be readily determined by those of skill in the art by reference to the present disclosure (including that incorporated by reference) and in concert with the ordinarily skilled artisan's general knowledge and skill in the art.

In that regard, pharmaceutical compositions containing a compound of the present disclosure (e.g., LR-90) or its pharmaceutically acceptable salts as the active ingredient can be prepared according to pharmaceutical compounding techniques. See, for example, [18]. Typically, an effective amount of the active ingredient will be admixed with a pharmaceutically acceptable carrier. The carrier may take a wide variety of forms depending on the form of preparation desired for administration, e.g., intravenous, oral or parenteral.

In embodiments, pharmaceutical compositions provided herein include an organic solvent including one or more of D-α-Tocopherol polyethylene glycol succinate (TPGS), poly-oxyethylene esters of 12-hydroxystearic acid (Solutol), macrogolgycerol hydroxystearate (Kolliphor RH40), Labrafac, or a cyclodextrin. In embodiments, the organic solvent includes D-α-Tocopherol polyethylene glycol succinate (TPGS). In embodiments, the organic solvent includes polyoxyethylene esters of 12-hydroxystearic acid (Solutol). In embodiments, the organic solvent includes macrogolgycerol hydroxystearate (Kolliphor RH40). In embodiments, the organic solvent includes Labrafac. In embodiments, the organic solvent includes a cyclodextrin.

In embodiments, pharmaceutical compositions provided herein include a cyclodextrin, where the cyclodextrin is 2-hydroxypropyl-beta-cyclodextrin (HPβCD).

In embodiments, pharmaceutical compositions provided herein include 2-hydroxypropyl-beta-cyclodextrin (HPβCD), where the concentration of HPβCD is from about 10% to about 40%. In embodiments, pharmaceutical compositions provided herein include 2-hydroxypropyl-beta-cyclodextrin (HPβCD), where the concentration of HPβCD is from about 15% to about 35%. In embodiments, pharmaceutical compositions provided herein include 2-hydroxypropyl-beta-cyclodextrin (HPβCD), where the concentration of HPβCD is from about 20% to about 30%. In embodiments, pharmaceutical compositions provided herein include 2-hydroxypropyl-beta-cyclodextrin (HPβCD), where the concentration of HPβCD is about 10%. In embodiments, pharmaceutical compositions provided herein include 2-hydroxypropyl-beta-cyclodextrin (HPβCD), where the concentration of HPβCD is about 11%. In embodiments, pharmaceutical compositions provided herein include 2-hydroxypropyl-beta-cyclodextrin (HPβCD), where the concentration of HPβCD is about 12%. In embodiments, pharmaceutical compositions provided herein include 2-hydroxypropyl-beta-cyclodextrin (HPβCD) where the concentration of HPβCD is about 13%. In embodiments, pharmaceutical compositions provided herein include 2-hydroxypropyl-beta-cyclodextrin (HPβCD), where the concentration of HPβCD is about 14%. In embodiments, pharmaceutical compositions provided herein include 2-hydroxypropyl-beta-cyclodextrin (HPβCD), where the concentration of HPβCD is about 15%. In embodiments, pharmaceutical compositions provided herein include 2-hydroxypropyl-beta-cyclodextrin (HPβCD), where the concentration of HPβCD is about 16%. In embodiments, pharmaceutical compositions provided herein include 2-hydroxypropyl-beta-cyclodextrin (HPβCD), where the concentration of HPβCD is about 17%. In embodiments, pharmaceutical compositions provided herein include 2-hydroxypropyl-beta-cyclodextrin (HPβCD), where the concentration of HPβCD is about 18%. In embodiments, pharmaceutical compositions provided herein include 2-hydroxypropyl-beta-cyclodextrin (HPβCD), where the concentration of HPβCD is about 19%. In embodiments, pharmaceutical compositions provided herein include 2-hydroxypropyl-beta-cyclodextrin (HPβCD), where the concentration of HPβCD is about 20%, about 21%. In embodiments, pharmaceutical compositions provided herein include 2-hydroxypropyl-beta-cyclodextrin (HPβCD), where the concentration of HPβCD is about 22%. In embodiments, pharmaceutical compositions provided herein include 2-hydroxypropyl-beta-cyclodextrin (HPβCD), where the concentration of HPβCD is about 23%. In embodiments, pharmaceutical compositions provided herein include 2-hydroxypropyl-beta-cyclodextrin (HPβCD), where the concentration of HPβCD is about 24%. In embodiments, pharmaceutical compositions provided herein include 2-hydroxypropyl-beta-cyclodextrin (HPβCD), where the concentration of HPβCD is about 25%. In embodiments, pharmaceutical compositions provided herein include 2-hydroxypropyl-beta-cyclodextrin (HPβCD), where the concentration of HPβCD is about 26%. In embodiments, pharmaceutical compositions provided herein include 2-hydroxypropyl-beta-cyclodextrin (HPβCD), where the concentration of HPβCD is about 27%. In embodiments, pharmaceutical compositions provided herein include 2-hydroxypropyl-beta-cyclodextrin (HPβCD), where the concentration of HPβCD is about 28%. In embodiments, pharmaceutical compositions provided herein include 2-hydroxypropyl-beta-cyclodextrin (HPβCD), where the concentration of HPβCD is about 29%. In embodiments, pharmaceutical compositions provided herein include 2-hydroxypropyl-beta-cyclodextrin (HPβCD), where the concentration of HPβCD is about 30%. In embodiments, pharmaceutical compositions provided herein include 2-hydroxypropyl-beta-cyclodextrin (HPβCD), where the concentration of HPβCD is about 31%. In embodiments, pharmaceutical compositions provided herein include 2-hydroxypropyl-beta-cyclodextrin (HPβCD), where the concentration of HPβCD is about 32%. In embodiments, pharmaceutical compositions provided herein include 2-hydroxypropyl-beta-cyclodextrin (HPβCD), where the concentration of HPβCD is about 33%. In embodiments, pharmaceutical compositions provided herein include 2-hydroxypropyl-beta-cyclodextrin (HPβCD), where the concentration of HPβCD is about 34%. In embodiments, pharmaceutical compositions provided herein include 2-hydroxypropyl-beta-cyclodextrin (HPβCD), where the concentration of HPβCD is about 35%. In embodiments, pharmaceutical compositions provided herein include 2-hydroxypropyl-beta-cyclodextrin (HPβCD), where the concentration of HPβCD is about 36%. In embodiments, pharmaceutical compositions provided herein include 2-hydroxypropyl-beta-cyclodextrin (HPβCD), where the concentration of HPβCD is about 37%. In embodiments, pharmaceutical compositions provided herein include 2-hydroxypropyl-beta-cyclodextrin (HPβCD), where the concentration of HPβCD is about 38%. In embodiments, pharmaceutical compositions provided herein include 2-hydroxypropyl-beta-cyclodextrin (HPβCD), where the concentration of HPβCD is about 39%. In embodiments, pharmaceutical compositions provided herein include 2-hydroxypropyl-beta-cyclodextrin (HPβCD), where the concentration of HPβCD is about 40%.

In embodiments, pharmaceutical compositions provided herein include an organic solvent including HPβCD at a concentration of about 20%.

In embodiments, the pharmaceutical compositions provided herein have a pH from about 7 to about 10. In embodiments, the pharmaceutical compositions provided herein have a pH from about 7.1 to about 9.9. In embodiments, the pharmaceutical compositions provided herein have a pH from about 7.2 to about 9.8. In embodiments, the pharmaceutical compositions provided herein have a pH from about 7.3 to about 9.7. In embodiments, the pharmaceutical compositions provided herein have a pH from about 7.4 to about 9.6. In embodiments, the pharmaceutical compositions provided herein have a pH from about 7.5 to about 9.5. In embodiments, the pharmaceutical compositions provided herein have a pH from about 7.6 to about 9.4. In embodiments, the pharmaceutical compositions provided herein have a pH from about 7.7 to about 9.3. In embodiments, the pharmaceutical compositions provided herein have a pH from about 7.8 to about 9.2. In embodiments, the pharmaceutical compositions provided herein have a pH from about 7.9 to about 9.1. In embodiments, the pharmaceutical compositions provided herein have a pH from about 8 to about 9. In embodiments, the pharmaceutical compositions provided herein have a pH from about 8.1 to about 8.9. In embodiments, the pharmaceutical compositions provided herein have a pH from about 8.2 to about 8.8. In embodiments, the pharmaceutical compositions provided herein have a pH from about 8.3 to about 8.7. In embodiments, the pharmaceutical compositions provided herein have a pH from about 8.4 to about 8.6. In embodiments, the pharmaceutical compositions provided herein have a pH of about 7. In embodiments, the pharmaceutical compositions provided herein have a pH of about 7.5. In embodiments, the pharmaceutical compositions provided herein have a pH of about 8. In embodiments, the pharmaceutical compositions provided herein have a pH of about 8.5. In embodiments, the pharmaceutical compositions provided herein have a pH of about 9. In embodiments, the pharmaceutical compositions provided herein have a pH of about 9.5. In embodiments, the pharmaceutical compositions provided herein have a pH of about 10.

In embodiments, the pharmaceutical compositions provided herein have a pH from about 7.5 to about 8.5. In embodiments, the pharmaceutical compositions provided herein have pH of about 8.

In embodiments, the pharmaceutical compositions provided herein LR-90 present in a concentration of about 5 to about 15 mg/ml. In embodiments, the pharmaceutical compositions provided herein LR-90 present in a concentration of about 5 to about 15 mg/ml.

In embodiments, the pharmaceutical compositions provided herein include LR-90 present in a concentration of about 5 to about 15 mg/ml. In embodiments, the pharmaceutical compositions provided herein include LR-90 present in a concentration of about 5 to about 10 mg/ml.

In embodiments, the pharmaceutical compositions provided herein include LR-90 present in a concentration of about 6 to about 14 mg/ml. In embodiments, the pharmaceutical compositions provided herein include LR-90 present in a concentration of about 7 to about 13 mg/ml. In embodiments, the pharmaceutical compositions provided herein include LR-90 present in a concentration of about 8 to about 12 mg/ml. In embodiments, the pharmaceutical compositions provided herein include LR-90 present in a concentration of about 9 to about 11 mg/ml. In embodiments, the pharmaceutical compositions provided herein include LR-90 present in a concentration of about 5 mg/ml. In embodiments, the pharmaceutical compositions provided herein include LR-90 present in a concentration of about 6 mg/ml. In embodiments, the pharmaceutical compositions provided herein include LR-90 present in a concentration of about 7 mg/ml. In embodiments, the pharmaceutical compositions provided herein include LR-90 present in a concentration of about 8 mg/ml. In embodiments, the pharmaceutical compositions provided herein include LR-90 present in a concentration of about 9 mg/ml. In embodiments, the pharmaceutical compositions provided herein include LR-90 present in a concentration of about 10 mg/ml. In embodiments, the pharmaceutical compositions provided herein include LR-90 present in a concentration of about 11 mg/ml. In embodiments, the pharmaceutical compositions provided herein include LR-90 present in a concentration of about 12 mg/ml. In embodiments, the pharmaceutical compositions provided herein include LR-90 present in a concentration of about 13 mg/ml. In embodiments, the pharmaceutical compositions provided herein include LR-90 present in a concentration of about 14 mg/ml. In embodiments, the pharmaceutical compositions provided herein include LR-90 present in a concentration of about 15 mg/ml.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable for passage through the gastrointestinal tract, while at the same time allowing for passage across the blood brain barrier.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, stabilizing agents, buffers and the like. One particularly suitable stabilizing agent for the conotoxin peptides contemplated here is carboxymethyl cellulose. This agent may be particularly effective due to the excess positive charge of the contemplated conotoxin peptides. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of the present disclosure, generally speaking, maybe practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

Data can be obtained, including as described herein, from cell culture assays and animal studies, to formulate a suitable dosage range for humans. Dosage may be adjusted appropriately to achieve desired drug levels, locally or systemically. A suitable dose can be administered in multiple sub-doses according to a suitable dosing schedule, such as multiple doses per day, per week, per month, or as otherwise indicated. Dosages are generally initiated at lower levels and increased until desired effects are achieved.

Advantageously, the compositions are formulated as dosage units, each unit being adapted to supply a fixed dose of active ingredients. Tablets, coated tablets, capsules, ampoules and suppositories are examples of dosage forms according to the disclosure.

The active ingredient of a composition of the disclosure typically constitutes an effective amount, such as a therapeutically effective amount or a prophylactically effective amount. The exact individual dosages, as well as daily dosages, are determined according to standard medical principles under the direction of a physician or veterinarian for use humans or animals.

In embodiments, compositions provided herein include an effective amount of LR-90. In embodiments, an amount effective to treat or prevent chemotherapy-induced neuropathic pain is about 1 mg to about 100 mg, about 10 mg to about 90 mg, about 20 mg to about 80 mg, about 30 mg to about 70 mg, about 40 mg to about 60 mg, or about 50 mg of LR-90 per kilogram weight of subject. In embodiments, an effective amount is about 1 to about 10 mg, about 2 to about 9 mg, about 3 mg to about 8 mg, about 4 mg to about 7 mg, or about 5 to about 6 mg of LR-90 per kilogram weight of subject. In embodiments, an effective amount of LR-90 is about or at most about 0.5 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 20 mg, or more per kilogram weight of subject. In embodiments, the effective amount of LR-90 is about or at most about 20 mg. In embodiments, the effective amount of LR-90 is about or at most about 15 mg. In embodiments, the effective amount of LR-90 is about or at most about 14 mg. In embodiments, the effective amount of LR-90 is about or at most about 13 mg. In embodiments, the effective amount of LR-90 is about or at most about 12 mg. In embodiments, the effective amount of LR-90 is about or at most about 11 mg. In embodiments, the effective amount of LR-90 is about or at most about 10 mg. In embodiments, the effective amount of LR-90 is about or at most about 9 mg. In embodiments, the effective amount of LR-90 is about or at most about 8 mg. In embodiments, the effective amount of LR-90 is about or at most about 7 mg. In embodiments, the effective amount of LR-90 is about or at most about 6 mg. In embodiments, the effective amount of LR-90 is about or at most about 5 mg. In embodiments, an effective amount is about 1 to about 100 mg of LR-90 per kilogram weight of subject. In embodiments, an effective amount is about 1 to about 10 mg of LR-90 per kilogram weight of subject.

In embodiments, the compositions provided herein include a chemotherapeutic compound in an effective amount. In embodiments, the chemotherapeutic agent is an effective amount of a mitotic inhibitor.

Kits and Uses

In an aspect, provided herein are kits including a chemotherapeutic compound (e.g. a mitotic inhibitor) and methylene bis[4,4'-(2-chlorophenylureidophenoxyisobutyric acid)] (LR-90) or a pharmaceutically acceptable salt or derivative thereof. In embodiments, the kit comprises one or more compositions described herein. In embodiments, the kit comprises one or more components of any of the compositions described herein. Components of the various compositions may be supplied separately from one another, such as in different containers within the kit.

In embodiments, kits include a pharmaceutically acceptable carrier. In embodiments, the kits provided herein include a pharmaceutically acceptable carrier including an organic solvent according to any of the various embodiments described herein. In embodiments, the kits include organic solvent including a cyclodextrin. In embodiments, the kits include a cyclodextrin, wherein the cyclodextrin is 2-hydroxypropyl-beta-cyclodextrin (HPβCD).

In embodiments, provided herein are kits that include a pharmaceutically acceptable carrier including a concentration of HPβCD from about 10% to about 40%. In embodiments, kits include a pharmaceutically acceptable carrier including a concentration of HPβCD of about 20%.

In embodiments, provided herein are kits including a chemotherapeutic compound (e.g. a mitotic inhibitor) and methylene bis[4,4'-(2-chlorophenylureidophenoxyisobutyric acid)] (LR-90) or a pharmaceutically acceptable salt or derivative thereof, where the pH is from about 7 to about 10. In embodiments, provided herein are kits including a chemotherapeutic compound (e.g. a mitotic inhibitor) and methylene bis[4,4'-(2-chlorophenylureidophenoxyisobutyric acid)] (LR-90) or a pharmaceutically acceptable salt or derivative thereof, where the pH is from about 7.5 to about 8.5. In embodiments, provided herein are kits including a chemotherapeutic compound (e.g. a mitotic inhibitor) and methylene bis[4,4'-(2-chlorophenylureidophenoxyisobutyric acid)] (LR-90) or a pharmaceutically acceptable salt or derivative thereof, where the pH is about 8.

In embodiments, kits provided herein include LR-90 present in an amount effective to treat or prevent chemotherapy-induced neuropathic pain in a subject. In embodiments, kits provided herein include LR-90 in a concentration of about 5 to about 15 mg/ml. In embodiments, kits provided herein include LR-90 in a concentration of about 5 to about 10 mg/ml.

In embodiments, kits provided herein include a chemotherapeutic compound that is a mitotic inhibitor. In embodiments, the mitotic inhibitor is vincristine, vinblastine, etoposide, teniposide, ixabepilone, nocodazole, epothilone, vinorelbine, camptothecin, irinotecan, topotecan, amsacrine, or lamellarin D. In embodiments, the mitotic inhibitor is a taxane. In embodiments, the taxane is cabazitaxel, paclitaxel, 10-deacetylbaccatin III, baccatin III, paclitaxel C, 7-epipaclitaxel, or docetaxel. In embodiments, the taxane is albumin-bound paclitaxel.

Provided herein are uses of LR-90 or a pharmaceutically acceptable salt or derivative thereof in treating or preventing chemotherapy-induced neuropathic pain in a subject in need thereof. In embodiments, the LR-90 or pharmaceutically acceptable salt or derivative thereof is part of a composition (e.g., a pharmaceutical composition) as described herein. In embodiments, the kit includes a pharmaceutically acceptable carrier, such as an organic solvent, in accordance with any of the various compositions described herein. In embodiments, the kit includes a chemotherapeutic compound, such as a mitotic inhibitor, in accordance with any of the various compositions described herein.

EXAMPLES

Example 1. Evaluation of the Efficacy of Test Article LR-90 in Taxol Induced Model of Neuropathic Pain In this example, the effect of LR-90 on Taxol-induced neuropathic pain was evaluated in a rat model.

Neuropathic pain was induced by intraperitoneal administration of Taxol at a dose level of 6 mg/kg on study days 0-6 and 12 mg/kg on study days 7-12. Following injection of Taxol animals experienced pain as was assessed using the von Frey test. The development of neuropathic pain was confirmed by measuring mechanical allodynia (Von Frey test) on study day 13 (for inclusion) and on study day 14 (1 hour and 2 hour post dosing) and 24 hour post first dosing.

Treatment with Gabapentin at a dose level of 150 mg/kg (Group 2) statistically significantly reduced the neuropathic pain 1 hour and 2 hour post dosing on study day 14, compared to the vehicle group (Group 3): 55.75±2.78 grams vs. 14.06±1.80 grams for the vehicle, 2 hour post dosing on study day 14; $p<0.0001$.

Treatment with LR-90 at a dose level of 100 mg/kg (Group 4) statistically significantly reduced the neuropathic pain 1 hour and 2 hour post dosing on study day 14, compared to the vehicle group (Group 3): 32.56±7.56 grams vs. vehicle 14.06±1.80 grams for the vehicle, 2 hour post dosing on study day 14; $p<0.001$. There was a statistically significant difference in the mean withdrawal force threshold between animals treated with 150 mg/kg Gabapentin and 100 mg/kg LR-90, only 2 hours post dosing on study day 14: 55.75±2.78 g vs. 32.56±7.56 g; $p<0.0001$.

No significant effect on the sensitivity of the treated animals to mechanical stimulation was seen following treatment with lower doses of LR-90, 50 mg/kg or 25 mg/kg.

These results illustrate that acute treatment with LR-90 at dose level of 100 mg/kg was significantly effective in reducing neuropathic pain, caused by Taxol administration, as tested using the von-Frey test.

TABLE 1

Details of materials used in the study

| Materials | Name | Cat. No. | Lot. No. | MDB Int. No. | Supplier | Storage Conditions | Expiry Date |
|---|---|---|---|---|---|---|---|
| Test Item | LR-90 | NA | NA | TA-1710-091 | Sponsor | 2-8 °C | NA |
| Vehicle | Corn Oil | C8267 | MKCC0462 | R-1709-121 | Sigma | Room temperature | NA |
| | DMSO | D5879 | SHBH9944 | R-1709-120 | Sigma | Room temperature | NA |
| Positive Control | Gabapentin | 1287303 | R020J0 | R-1702-029 | MDB | 2-8 °C | NA |

TABLE 1-continued

| Details of materials used in the study | | | | | | | |
|---|---|---|---|---|---|---|---|
| Materials | Name | Cat. No. | Lot. No. | MDB Int. No. | Supplier | Storage Conditions | Expiry Date |
| Sensitizing Item | Taxol (Paclitaxel) | P-9600 | ASM-120 | R-1709-124 | MDB USA | −20 °C | NA |
| Solvent for Sensitizing Item | Saline | AWN1324 | J43374 | NA | Vetmarket | Room temperature | December 2017 |
| Euthanasia Item | Pentobarbital Sodium | NA | 170084 | R-1706-100 | Vetmarket | Room temperature | July 2018 |

A schematic depiction of taxol induction and treatment is illustrated in FIG. 1.

TABLE 2

| Experimental groups in the study | | | | | | | |
|---|---|---|---|---|---|---|---|
| Group No. | Group Size | Test Item | Dose (mg/kg) | Volume (ml/kg) | Route | Regime | Von Frey testing |
| 1 | N = 5 | Naive | N/A | N/A | N/A | N/A | Day −1: Baseline. Day 13: Inclusion. Day 14: 1 h and 2 h post dosing. Day 15: 24 h post dosing. |
| 2 | N = 8 (4)* | Gabapentin | 150 | 3 | IP | QD on study day 14 | |
| 3 | N = 8 (3)* | Vehicle 1 (Corn oil + 4% DMSO) | 0 | 10 | PO | QD on study days 14-25 | |
| 4 | N = 8 (3)* | LR-90 | 100 | 10 | PO | | |
| 5 | N = 8 (3)* | LR-90 | 50 | 10 | PO | | |

TABLE 2-continued

| Experimental groups in the study | | | | | | | |
|---|---|---|---|---|---|---|---|
| Group No. | Group Size | Test Item | Dose (mg/kg) | Volume (ml/kg) | Route | Regime | Von Frey testing |
| 6 | N = 8 (3)* | LR-90 | 25 | 10 | PO | | |

*Note:
At the end of the study (day 26) number of animals was as followed: Four rats in Gabapentin treated group (Group 2), three rats in Vehicle and LR-90 treated groups (Groups 3, 4, 5, 6).

Data Evaluation:

All data are presented as means f SEM. Each treatment group was compared to the Vehicle group using Two way ANOVA (for VF) followed by Tukey post-test (GraphPad). Vehicle group is compared to naïve group using T-test. A p value <0.05 is considered to represent a significant difference.

Animal Care and Use Treatment:

This study was performed following approval of an application form submitted to the Committee for Ethical Conduct in the Care and Use of Laboratory Animals that stated that the study complied with the rules and regulations set forth.

Results

Figure 2:
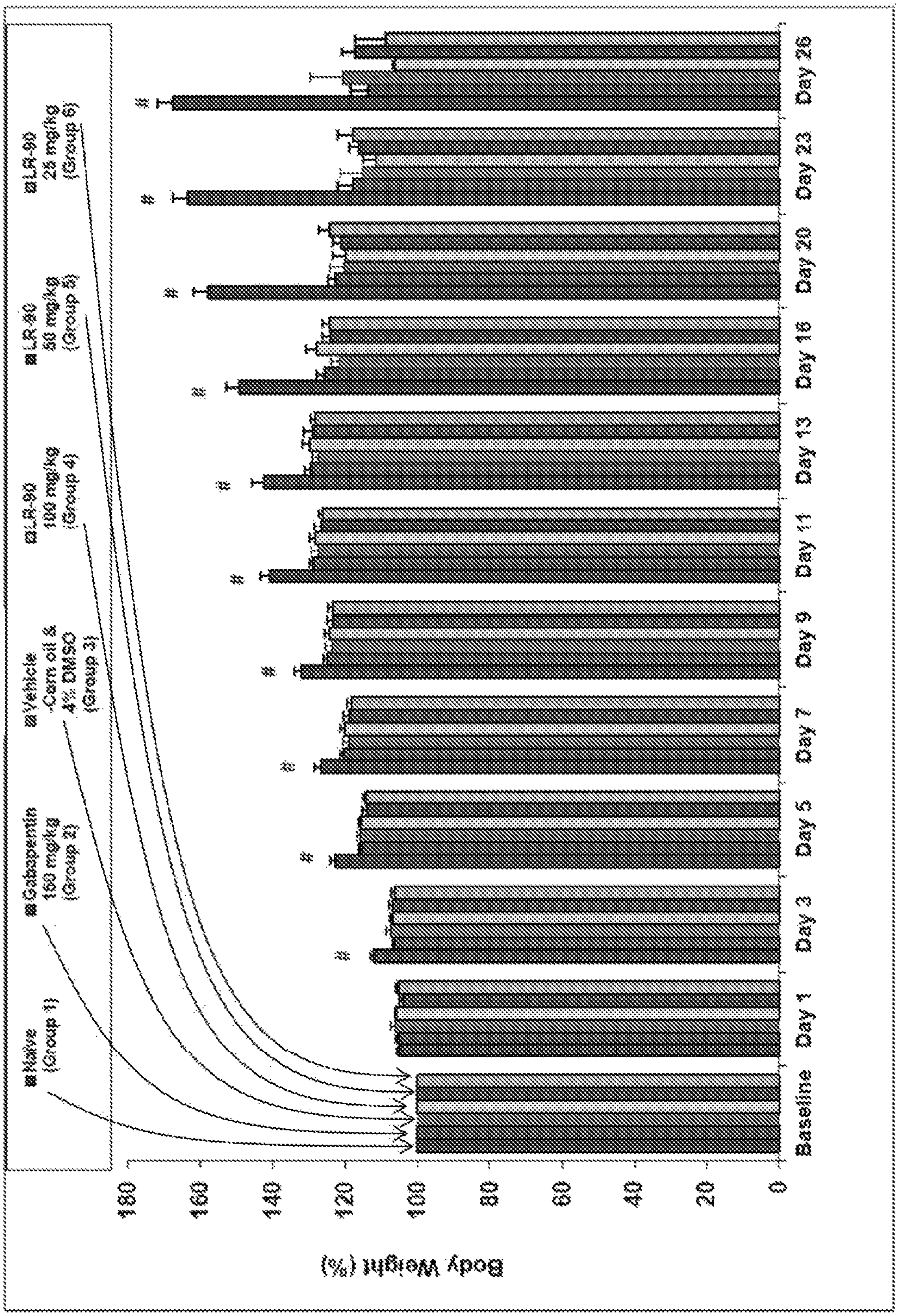
FIG. 2 is a bar graph illustrating mean group body weight (%), according to an example. #p<0.05 Naïve vs. Vehicle using T-test.

Mean Body Weight is presented in Tables 2,3 and FIG. 2.

TABLE 2(a)

| Mean group body weight (g) | | | | | | | | | | | | | |
|---|---|---|---|---|---|---|---|---|---|---|---|---|---|
| Group | | Baseline | | Day 1 | | Day 3 | | Day 5 | | Day 7 | | Day 9 | |
| # | Treatment | Mean | SEM | Mean | SEM | Mean | SEM | Mean | SEM | Mean | SEM | Mean | SEM |
| 1 | Naïve (Group 1) | 217.40 | 2.66 | 228.20 | 3.83 | 243.60 | 4.34 | 266.60 | 5.25 | 275.20 | 6.78 | 287.20 | 6.89 |
| 2 | Gabapentin 150 mg/kg (Group 2) | 223.38 | 3.04 | 235.25 | 3.39 | 237.50 | 3.77 | 258.13 | 4.27 | 269.25 | 4.95 | 278.75 | 5.45 |
| 3 | Vehicle-Corn oil & 4% DMSO (Group 3) | 220.75 | 2.60 | 234.38 | 3.78 | 237.13 | 4.11 | 255.50 | 3.69 | 262.88 | 4.65 | 272.38 | 5.19 |
| 4 | LR-90 100 mg/kg (Group 4) | 222.63 | 1.45 | 235.50 | 2.13 | 237.63 | 2.08 | 257.25 | 2.27 | 267.25 | 3.43 | 276.50 | 3.64 |
| 5 | LR-90 50 mg/kg (Group 5) | 225.88 | 2.46 | 234.38 | 2.56 | 241.63 | 3.88 | 257.50 | 4.47 | 268.63 | 5.48 | 278.38 | 5.87 |
| 6 | LR-90 25 mg/kg (Group 6) | 223.50 | 3.06 | 235.00 | 3.09 | 237.50 | 3.93 | 255.50 | 3.75 | 264.30 | 5.08 | 275.88 | 5.47 |

TABLE 2(b)

| Mean group body weight (g) | | | | | | | | | | | | | |
|---|---|---|---|---|---|---|---|---|---|---|---|---|---|
| Group | | Day 11 | | Day 13 | | Day 16 | | Day 20 | | Day 23 | | Day 26 | |
| # | Treatment | Mean | SEM | Mean | SEM | Mean | SEM | Mean | SEM | Mean | SEM | Mean | SEM |
| 1 | Naïve (Group 1) | 306.00 | 8.58 | 309.80 | 9.00 | 324.40 | 9.87 | 343.00 | 10.79 | 355.00 | 11.48 | 364.60 | 11.31 |
| 2 | Gabapentin 150 mg/kg (Group 2) | 287.63 | 5.48 | 289.50 | 5.72 | 281.00 | 7.35 | 274.38 | 6.11 | 263.38 | 9.36 | 247.7[5 | 13.46 |
| 3 | Vehicle-Corn oil & 4% DMSO (Group 3) | 281.13 | 5.49 | 280.75 | 5.40 | 268.13 | 5.66 | 265.38 | 8.70 | 251.83 | 13.89 | 266.67 | 21.40 |
| 4 | LR-90 100 mg/kg (Group 4) | 285.00 | 4.26 | 288.75 | 4.48 | 284.75 | 6.32 | 266.63 | 7.95 | 249.00 | 8.42 | 234.00[ | 2.08 |
| 5 | LR-00 50 mg/kg (Group 5) | 286.13 | 6.51 | 291.38 | 7.30 | 280.13 | 6.20 | 273.75 | 6.72 | 264.29 | 7.13 | 266.67 | 8.84 |
| 6 | LR-90 25 mg/kg (Group 6) | 282.38 | 5.24 | 286.75 | 5.38 | 277.50 | 7.05 | 277.63 | 8.42 | 263.63 | 10.86 | 239.00 | 20.74 |

TABLE 3(a)

| Mean group body weight (% from baseline) | | | | | | | | | | | | | |
|---|---|---|---|---|---|---|---|---|---|---|---|---|---|
| Group | | Baseline | | Day 1 | | Day 3 | | Day 5 | | Day 7 | | Day 9 | |
| # | Treatment | Mean | SEM | Mean | SEM | Mean | SEM | Mean | SEM | Mean | SEM | Mean | SEM |
| 1 | Naïve (Group 1) | 100.00 | 0.00 | 104.95 | 0.74 | 112.03[#] | 0.98 | 122.61[#] | 1.47 | 126.53[#] | 1.57 | 132.06[#] | 2.08 |
| 2 | Gabapentin 150 mg/kg (Group 2) | 100 00 | 0.00 | 105.31 | 0.39 | 106.31 | 0.53 | 115.54 | 0.77 | 120.50 | 1.02 | 124.74 | 1.21 |
| 3 | Vehicle-Corn oil & 4% DMSO (Group 3) | 100.00 | 0.00 | 106.17 | 1.13 | 107.40 | 1.14 | 115.75 | 1.09 | 119.07 | 1.46 | 123.39 | 1.93 |
| 4 | LR-90 100 mg/kg (Group 4) | 100.00 | 0.00 | 105.77 | 0.43 | 106.74 | 0.72 | 115.56 | 0.77 | 120.04 | 1.24 | 124.20 | 1.44 |
| 5 | LR-90 50 mg/kg (Group 5) | 100.00 | 0.00 | 103.80 | 1.09 | 106.95 | 0.90 | 113.97 | 1.20 | 118.88 | 1.64 | 123.18 | 1.67 |
| 6 | LR-90 25 mg/kg (Group 6) | 100.00 | 0.00 | 105.16 | 0.63 | 106.26 | 0.87 | 114.32 | 0.65 | 118.31 | 1.14 | 123.38 | 1.13 |

[#]p < 0.05 Naïve vs. Vehicle using T-test.

TABLE 3(b)

| Mean group body weight (% from baseline) | | | | | | | | | | | | | |
|---|---|---|---|---|---|---|---|---|---|---|---|---|---|
| Group | | Day 11 | | Day 13 | | Day 16 | | Day 20 | | Day 23 | | Day 26 | |
| # | Treatment | Mean | SEM | Mean | SEM | Mean | SEM | Mean | SEM | Mean | SEM | Mean | SEM |
| 1 | Naïve (Group 1) | 140.68[#] | 2.81 | 142.43[#] | 3.10 | 149.15[#] | 3.54 | 157.70[#] | 4.05 | 163.22[#] | 4.28 | 167.63[#] | 4.16 |
| 2 | Gabapentin 150 mg/kg (Group 2) | 128.71 | 1.20 | 129.56 | 1.44 | 125.68 | 2.01 | 122.79 | 1.85 | 117.94 | 4.04 | 113.52 | 5.04 |
| 3 | Vehicle-Corn oil & 4% DMSO (Group 3) | 127.34 | 1.88 | 127.17 | 1.81 | 121.50 | 2.43 | 120.24 | 3.76 | 115.10 | 6.12 | 120.58 | 8.99 |

TABLE 3(b)-continued

| Mean group body weight (% from baseline) | | | | | | | | | | | | | |
|---|---|---|---|---|---|---|---|---|---|---|---|---|---|
| Group | | Day 11 | | Day 13 | | Day 16 | | Day 20 | | Day 23 | | Day 26 | |
| # | Treatment | Mean | SEM | Mean | SEM | Mean | SEM | Mean | SEM | Mean | SEM | Mean | SEM |
| 4 | LR-90 100 mg/kg (Group 4) | 128.01 | 1.67 | 129.71 | 1.87 | 127.91 | 2.73 | 119.75 | 3.38 | 111.34 | 3.50 | 106.04 | 0.85 |
| 5 | LR-90 50 mg/kg (Group 5) | 126.60 | 1.94 | 128.91 | 2.32 | 123.98 | 2.10 | 121.18 | 2.05 | 116.09 | 2.66 | 117.29 | 3.50 |
| 6 | LR-90 25 mg/kg (Group 6) | 126.30 | 0.96 | 128.26 | 1.14 | 124.11 | 2.28 | 124.18 | 3.14 | 117.84 | 4.09 | 108.59 | 8.65 |

#p < 0.05 Naïve vs. Vehicle using T-test.

The response to tactile allodynia was evaluated using the Von Frey apparatus (Touch Test®). The rat was placed in an enclosure and positioned on a metal mesh surface, but allowed to move freely. A set of dull monofilaments provide an increasing force was applied on the animal plantar surface of the paw. The lowest force requires for animal paw withdrawal was recorded. Low force values recorded in this test indicate a painful state.

TABLE 4

| The mean Von Frey force required for withdrawal (g). | | | | | | | | | | | |
|---|---|---|---|---|---|---|---|---|---|---|---|
| Group | | Baseline | | Day 13 pre dosing | | Day 14 1 hour post dosing | | Day 14 2 hours post dosing | | Day 15 24 hours post dosing | |
| # | Treatment | Mean | SEM | Mean | SEM | Mean | SEM | Mean | SEM | Mean | SEM |
| 1 | Naïve (Group 1) | 56.60 | 3.40 | 49.80# | 4.16 | 46.40# | 6.36 | 49.80# | 4.16 | 49.80# | 4.16 |
| 2 | Gabapentin 150 mgikg (Group 2) | 57.88 | 2.13 | 9.81 | 0.76 | 45.13**** | 5.02 | 55.75**** $$$$ | 2.78 | 19.56 | 3.92 |
| 3 | Vehicle-Corn oil & 4% DMSO (Group 3) | 60.00 | 0.00 | 10.06 | 0.78 | 11.94 | 0.87 | 14.06 | 1.80 | 20.50 | 1.47 |
| 4 | LR-90 100 mg/kg (Group 4) | 57.88 | 2.13 | 10.06 | 0.78 | 34.69**** | 5.12 | 32.56*** | 7.56 | 26.25 | 3.78 |
| 5 | LR-90 50 mg/kg (Group 5) | 60.00 | 0.00 | 9.81 | 0.74 | 17.38 | 3.22 | 22.13 | 4.42 | 16.75 | 1.96 |
| 6 | LR-90 25 mg/kg (Group 6) | 60.00 | 0.00 | 9.81 | 0.81 | 21.88 | 2.29 | 17.31 | 1.51 | 14.13 | 1.10 |

***p < 0.001 vs. Vehicle using two way ANOVA test followed by a Tukey test.
****p < 0.0001 vs. Vehicle using two way ANOVA test followed by a Tukey test.
$$$$ p < 0.0001 vs. LR-90 (100 mg/kg; Group 4) using two way ANOVA test followed by a Tukey test.
#p < 0.05 Naïve vs. Vehicle using T-test.

Figure 3:
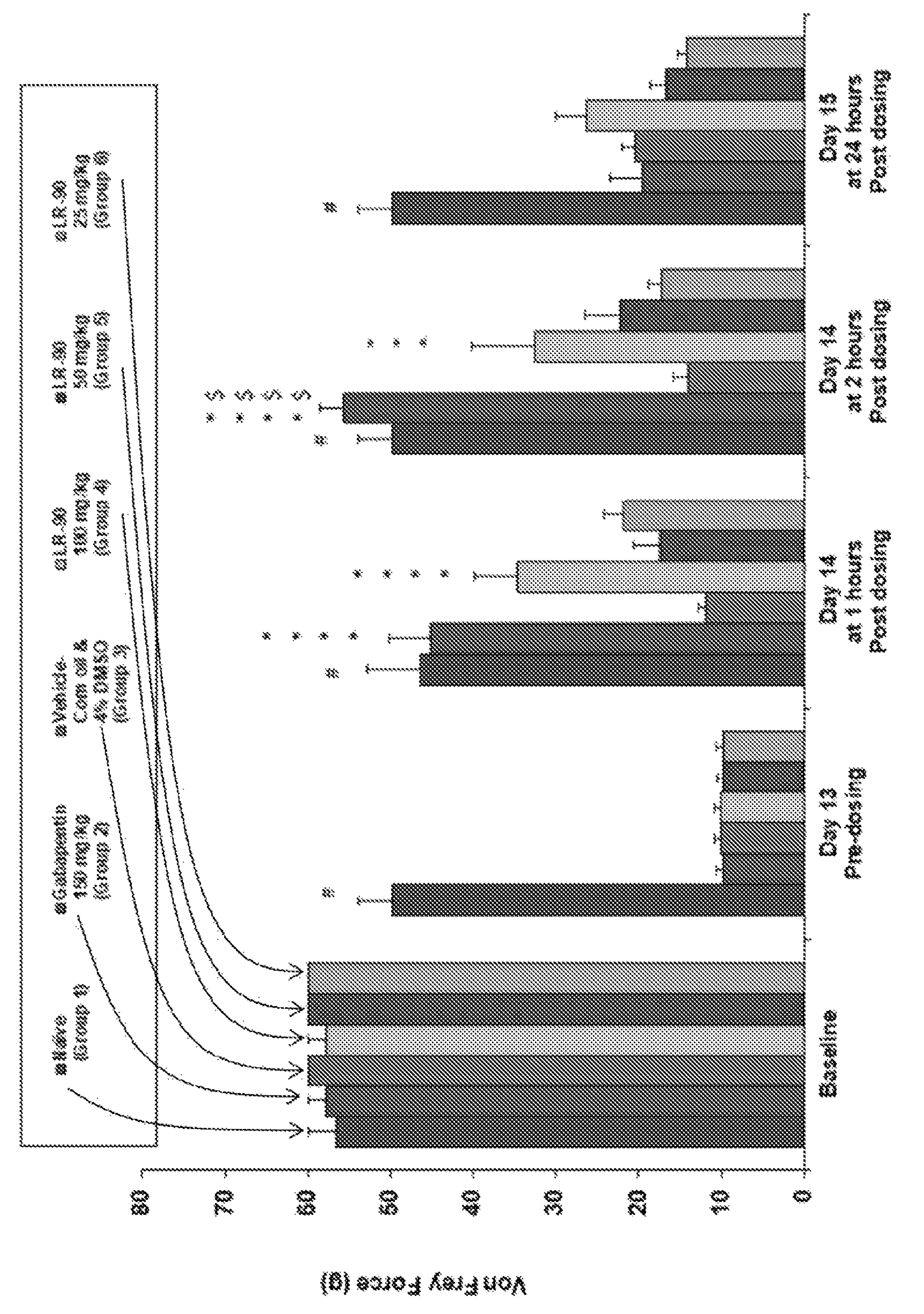
FIG. 3 is a bar graph of example results for mean Von Frey force required for withdrawal (g). *p<0.001 vs. Vehicle using two way ANOVA test followed by a Tukey test. **p<0.0001 vs. Vehicle using two way ANOVA test followed by a Tukey test. $$$$ p<0.0001 vs. LR-90 (100 mg/kg; Group 4) using two way ANOVA test followed by a Tukey test. #p<0.05 Naïve vs. Vehicle using T-test.

Example results for the mean Von Frey force required for withdrawal are also illustrated in FIG. 3.

TABLE 5

| Survival of animals during the study Survival (%) | | | | | | | | | | | | | |
|---|---|---|---|---|---|---|---|---|---|---|---|---|---|
| | Survived Animals in % Study Days | | | | | | | | | | | | | 
| Treatment and Group | 13 | 14 | 15 | 16 | 17 | 18 | 19 | 20 | 21 | 22 | 23 | 24 | 25 | 28 |
| Naïve (Group 1) | 100 | 100 | 100 | 100 | 100 | 100 | 100 | 100 | 100 | 100 | 100 | 100 | 100 | 100 |
| Gabapentin 150 mg/kg (Group 2) | 100 | 100 | 100 | 100 | 100 | 100 | 100 | 100 | 100 | 100 | 100 | 88 | 63 | 50 |

TABLE 5-continued

| Survival of animals during the study Survival (%) | | | | | | | | | | | | | | |
|---|---|---|---|---|---|---|---|---|---|---|---|---|---|---|
| | Survived Animals in % Study Days | | | | | | | | | | | | | |
| Treatment and Group | 13 | 14 | 15 | 16 | 17 | 18 | 19 | 20 | 21 | 22 | 23 | 24 | 25 | 28 |
| Vehicle-Corn oil & 4% DMSO (Group 3) | 100 | 100 | 100 | 100 | 100 | 100 | 100 | 100 | 100 | 75 | 63 | 63 | 38 | 38 |
| LR-90 100 mg/kg (Group 4) | 100 | 100 | 100 | 100 | 100 | 100 | 100 | 100 | 100 | 100 | 88 | 63 | 38 | 38 |
| LR-90 50 mg/kg (Group 5) | 100 | 100 | 100 | 100 | 100 | 100 | 100 | 100 | 100 | 88 | 88 | 50 | 50 | 38 |
| LR-90 25 mg/kg (Group 6) | 100 | 100 | 100 | 100 | 100 | 100 | 100 | 100 | 100 | 100 | 100 | 100 | 75 | 38 |

Example 2. LR-90 Formulation and Stability Studies

Figure 4:
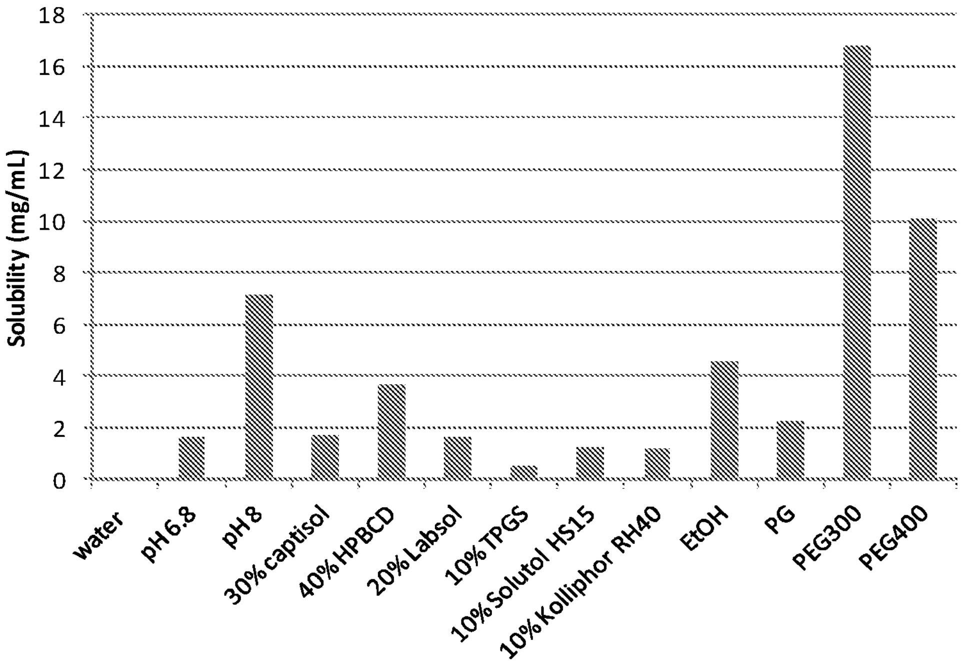
FIG. 4 is a bar graph showing the solubility of different LR-90 formulations.

In order to develop a vehicle formulation for LR-90 for use in humans, 15 different vehicles were tested to measure the solubility of the purified LR-90 (Table 6). FIG. 4 shows the solubility of the formulations.

TABLE 6

| Formulations tested | |
|---|---|
| Media | Solubility (mg/mL) |
| Water | ND |
| pH 6.8 | 1.67 |
| pH 8 | 7.12 |
| 30% Captisol in water (W/V) | 1.71 |
| 40% HPβCD in water (W/V) | 3.66 |
| 20% Labsol tn water (W/V) | 1.65 |
| 10% TPGS in water (W/V) | 0.56 |
| 10% Solutol in water (W/V) | 1.25 |
| 10% Kolliphor RH40 in water ((W/V) | 1.22 |
| DMA | >531.00 |
| DMSO | >258.50 |
| EtOH | >4.60 |
| PG | >2.27 |
| PEG300 | >16.79 |
| PEG400 | >10.10 |

LR-90 could be dissolved in 20% HPβCD in pH 8.0 buffer (w/v) to make a solution of concentration 5 or 10 mg/ml (drug target concentration). There was no degradation of the compound in 20% HPβCD solution at least for 24 hours (see Table 7, showing results as measured by HPLC area (%) for the indicated formulations).

TABLE 7

| Formulation stability | | |
|---|---|---|
| LR-90 Formulation | Initial Purity | Final Purity (24 hr) |
| 5 mg/ml | 99.21 | 99.20 |
| 10 mg/ml | 99.20 | 99.14 |

To test the stability in the acidic environment (simulated gastric fluid test) of 5 and 10 mg/ml of LR-90 in 20% h HPβCD in pH 8.0 buffer, the two concentrations were added into the equal volume of pH 1.2 buffer, mixed completely, and then observed under a polarized light microscope. Very little precipitation appeared about 60 min later in the formulation of 20% HPβCD in pH 8.0 buffer containing 10 mg/ml LR-90. However, no precipitation occurred after an hour for the same formulation containing 5 mg/ml LR-90 (data not shown). This suggests that LR-90 in 20% HPβCD solution was stable even in the acidic environment. Based on these results, pre-clinical development studies were performed using 5 or 10 mg LR-90 in 20% h HPβCD in pH 8.0 buffer.

Figure 5:
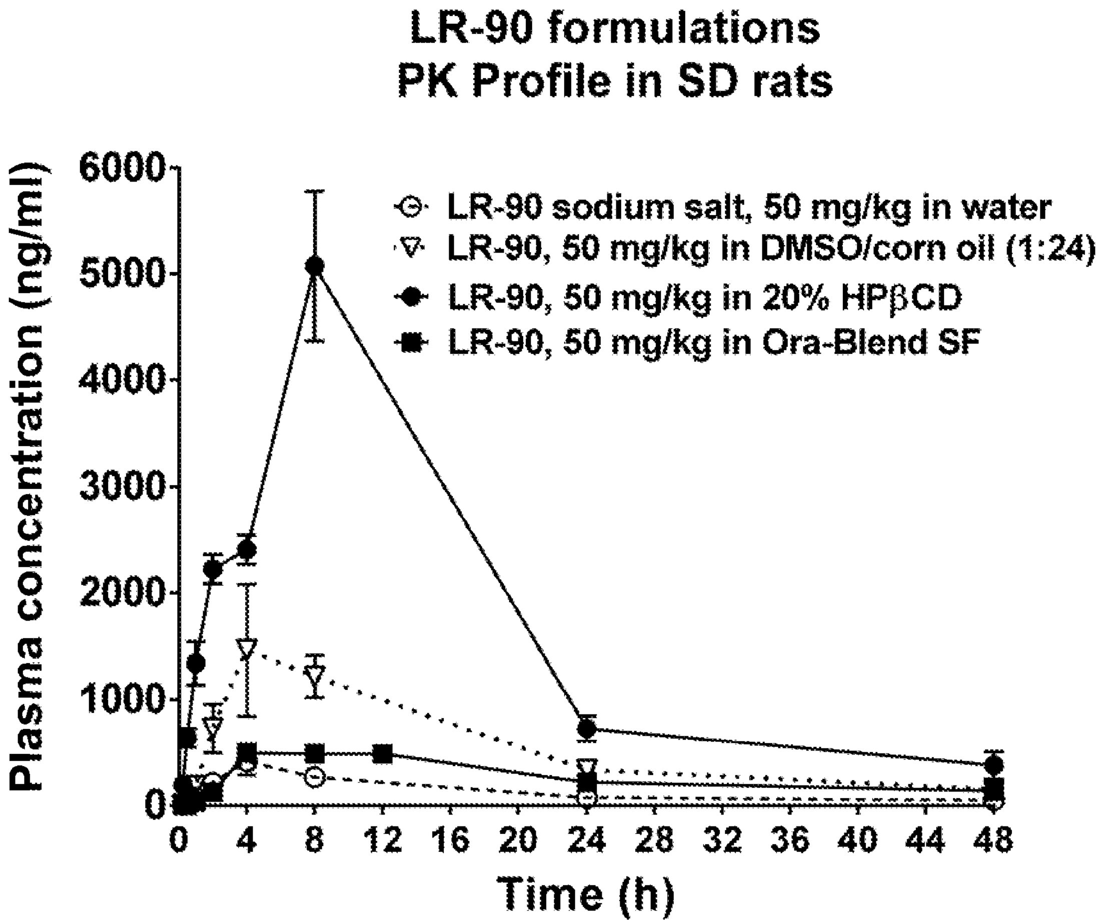
FIG. 5 shows the results of pharmacokinetic studies of LR-90 following a single oral administration to SD rats.

Example 3: Pharmacokinetic Studies of LR-90 Following a Single Oral Administration to SD Rats Pharmacokinetic studies of four different formulations of LR-90 were investigated. LR-90 either in salt formulation dissolved in water, in 4% DMSO in corn oil, in 20% HPβCD in pH 8.0 buffer, and in Ora-Blend SF was delivered at a dose of 50 mg/kg by oral gavage in Sprague-Dawley (SD) rats. Blood samples were collected at 0 min, 15 min, 30 min, 1 hr, 2 hr, 4 hr, 8 hr, 24 hr and 48 hr post-dosing. LR-90 level was determined in plasma by LC-MS/MS assay. The pharmacokinetic (PK) studies revealed that LR-90 in 20% HPβCD was superior all three other formulations (FIG. 5).

Behavioral Studies

Figure 6:
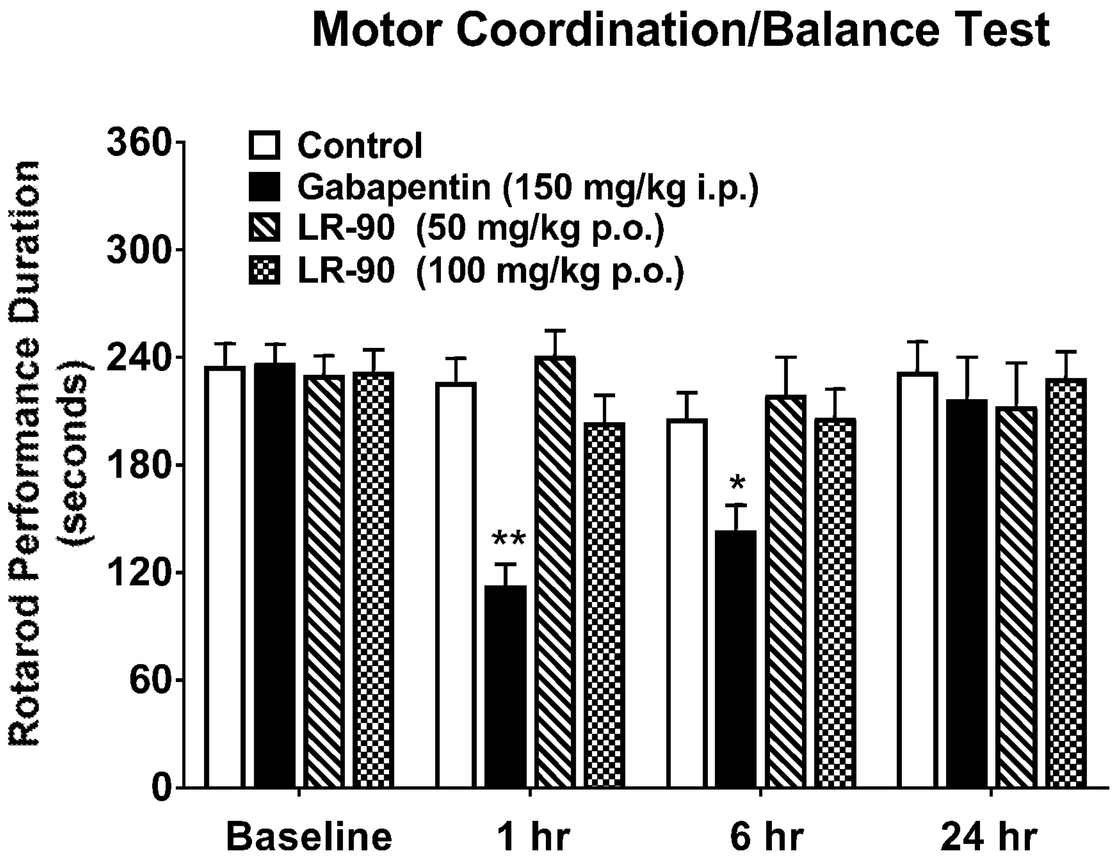
FIG. 6 is a bar graph of example results for motor coordination and balance studies of rats treated with example LR-90 formulations.

The objective of this study was to evaluate the potential CNS effects of LR-90 and gabapentin (the latter a widely used drug for neuropathic pain) in rats. LR-90 in 20% HPβCD formulation was delivered at a dose of 50 or 100 mg/kg by oral gavage and gabapentin (150 mg/kg) was delivered by i.p. injection. The rotarod test was employed to measure the CNS activity (motor coordination and balance) and the performance time was recorded at 0 (baseline), 1, 6 and 24 hr post-dose. Gabapentin significantly decreased the rotarod performance time at 1 and 6 hr post-dosing compared with vehicle control group. However, LR-90 did not show any significant effect on the rotarod performance at each time point, indicating that it has no potential CNS effect under the current dosing regimen. Illustrative results are shown in FIG. 6.

REFERENCES

1. Dougherty P M, Cata J P, Cordella J V, et al. Taxol-induced sensory disturbance is characterized by preferential impairment of myelinated fiber function in cancer patients. Pain. 2004; 109:132-42
2. van den Bent M J, van Raaij-van den Aarssen V J, Verweij J, et al. Progression of paclitaxel-induced neuropathy following discontinuation of treatment. Muscle Nerve. 1997; 20:750-2
3. Boyette-Davis J A, Cata J P, Zhang H, et al. Follow-up psychophysical studies in bortezomib-related chemoneuropathy patients. J Pain. 2011; 12:1017-24
4. Hershman D L, Lacchetti C, Dworkin R H, et al. Prevention and management of chemotherapy-induced peripheral neuropathy in survivors of adult cancers: American Society of Clinical Oncology clinical practice guideline. J Clin Oncol. 2014; 32:1941-67.
5. Sambrook, et al., Molecular Cloning: A Laboratory Manual (3rd Edition, 2001)
6. Sambrook, et al., Molecular Cloning: A Laboratory Manual (2nd Edition, 1989)
7. Maniatis et al., Molecular Cloning: A Laboratory Manual (1982); Ausubel et al.
8. Current Protocols in Molecular Biology (John Wiley and Sons, updated July 2008)
9. Short Protocols in Molecular Biology: A Compendium of Methods from Current Protocols in Molecular Biology, Greene Pub. Associates and Wiley-Interscience
10. Glover, DNA Cloning: A Practical Approach, vol. I & II (IRL Press, Oxford, 1985)
11. Anand, Techniques for the Analysis of Complex Genomes, (Academic Press, New York, 1992)
12. Hames, B. S. Higgins, S. Transcription and Translation (Eds., 1984)
13. Berge et al., "Pharmaceutical Salts", *Journal of Pharmaceutical Science,* 1977, 66, 1-19.
14. Soriano Fg, Pacher P, Mabley J, Liaudet L, Szabo C. Rapid reversal of the diabetic endothelial dysfunction by pharmacological inhibition of poly(ADP-ribose) polymerase. Circ Res. 2001a; 89:684-91
15. Pacher P, Liaudet L, Bai P, Virag L, Mabley Jg, Hasko G, Szabo C. Activation of poly(ADP-ribose) polymerase contributes to development of doxorubicin-induced heart failure. J Pharmacol Exp Ther. 2002b; 300:862-7.
16. U.S. Pat. Re. 36,397
17. Bowman et al. Br J Cancer. 2001 Jan. 5; 84(1):106-12.
18. Remington's Pharmaceutical Sciences, 18th Ed. (1990, Mack Publishing Co., Easton, Pa.

EMBODIMENTS

Embodiment 1. A method of treating chemotherapy-induced neuropathic pain in a subject in need thereof, wherein said method comprises administering to the subject an effective amount of methylene bis[4,4'-(2-chlorophenylureidophenoxyisobutyric acid)] (LR-90) or a pharmaceutically acceptable salt or derivative thereof.

Embodiment 2. A method of preventing chemotherapy-induced neuropathic pain in a subject in need thereof, wherein said method comprises administering to the subject an effective amount of methylene bis[4,4'-(2-chlorophenylureidophenoxyisobutyric acid)] (LR-90) or a pharmaceutically acceptable salt or derivative thereof.

Embodiment 3. The method of embodiments 1 or 2, wherein LR-90 is formulated in a pharmaceutically acceptable carrier.

Embodiment 4. The method of embodiment claim 3, wherein the pharmaceutically acceptable carrier comprises an organic solvent.

Embodiment 5. The method of embodiment 4, wherein the organic solvent comprises one or more of D-α-Tocopherol polyethylene glycol succinate (TPGS), poly-oxyethylene esters of 12-hydroxystearic acid (Solutol), macrogolglycerol hydroxystearate (Kolliphor RH40), Labrafac, or a cyclodextrin.

Embodiment 6. The method of embodiment 5, wherein the organic solvent comprises a cyclodextrin.

Embodiment 7. The method of embodiment 6, wherein the cyclodextrin is 2-hydroxypropyl-beta-cyclodextrin (HPβCD).

Embodiment 8. The method of embodiment 7, wherein the concentration of HPβCD is from about 10% to about 40%.

Embodiment 9. The method of claim 8, wherein the concentration of HPβCD is about 20%.

Embodiment 10. The method of any one of embodiments 1-9, wherein the pH is from about 7 to about 10.

Embodiment 11. The method of embodiment 10, wherein the pH is from about 7.5 to about 8.5.

Embodiment 12. The method of embodiment 11, wherein the pH is about 8.

Embodiment 13. The method of any of embodiments 1-12, wherein the subject has cancer and is receiving or has been prescribed treatment with a chemotherapeutic compound.

Embodiment 14. The method of embodiment 13, wherein the cancer is a solid tumor cancer.

Embodiment 15. The method of any one of embodiments 13 or 14, wherein the cancer is prostate cancer, hormone-refractory prostate cancer, ovarian cancer, breast cancer, head and neck cancer, stomach cancer, lung cancer, non-small cell lung cancer, Kaposi sarcoma, cervical cancer, pancreatic cancer, melanoma, esophageal cancer.

Embodiment 16. The method of any one of embodiments 13-15 wherein the chemotherapeutic compound is a mitotic inhibitor.

Embodiment 17. The method of embodiment 16, wherein the mitotic inhibitor is vincristine, vinblastine, etoposide, teniposide, ixabepilone, nocodazole, epothilone, vinorelbine, camptothecin, irinotecan, topotecan, amsacrine, or lamellarin D.

Embodiment 18. The method of embodiment 16, wherein the mitotic inhibitor is a taxane.

Embodiment 19. The method of embodiment 18, wherein the taxane is cabazitaxel, paclitaxel, 10-deacetylbaccatin III, baccatin III, paclitaxel C, 7-epipaclitaxel, or docetaxel.

Embodiment 20. The method of embodiment 19, wherein the taxane is albumin-bound paclitaxel.

Embodiment 21. The method of any one of embodiments 1-19 wherein the subject is receiving or has been prescribed treatment with cisplatin, dexamethasone, doxorubicin, etoposide, bortezomib, or vinblastine.

Embodiment 22. The method of any one of embodiments 1-21, wherein the effective amount is about 1-100 mg/kg.

Embodiment 23. The method of embodiment 22, wherein the effective amount is about 1-10 mg/kg.

Embodiment 24. The method of any one of embodiments 13-22, wherein LR-90 is administered before, together with, concurrently with, or after the chemotherapeutic compound.

Embodiment 25. The method of any one of embodiments 13-24, wherein LR-90 is administered orally and the chemotherapeutic compound is administered intravenously.

Embodiment 26. A composition comprising a chemotherapeutic compound and LR-90 or a pharmaceutically acceptable salt or derivative thereof.

Embodiment 27. The composition of embodiment 26, which is a pharmaceutical composition further comprising a pharmaceutically acceptable carrier.

Embodiment 28. The composition of embodiment 27, wherein the pharmaceutical composition comprises an organic solvent.

Embodiment 29. The composition of embodiment 28, wherein the organic solvent comprises one or more of D-α-Tocopherol polyethylene glycol succinate (TPGS), poly-oxyethylene esters of 12-hydroxystearic acid (Solutol), macrogolgycerol hydroxystearate (Kolliphor RH40), Labrafac, or a cyclodextrin.

Embodiment 30. The composition of embodiment 29, wherein the organic solvent comprises a cyclodextrin.

Embodiment 31. The composition of embodiment 30, wherein the cyclodextrin is 2-hydroxypropyl-beta-cyclodextrin (HPβCD).

Embodiment 32. The composition of embodiment 31, wherein the concentration of HPβCD is from about 10% to about 40%.

Embodiment 33. The composition of embodiment 32, wherein the concentration of HPβCD is about 20%.

Embodiment 34. The composition of any one of embodiments 26-33, wherein the pH is from about 7 to about 10.

Embodiment 35. The composition of embodiment 34, wherein the pH is from about 7.5 to about 8.5.

Embodiment 36. The composition of embodiment 35, wherein the pH is about 8.

Embodiment 37. The composition of any one of embodiments 26-36, wherein the LR-90 is present in an amount effective to treat or prevent chemotherapy-induced neuropathic pain in a subject.

Embodiment 38. The composition of embodiment 37, wherein LR-90 is present in a concentration of about 5 to about 15 mg/ml.

Embodiment 39. The composition of embodiment 38, wherein LR-90 is present in a concentration of about 5 to about 10 mg/ml.

Embodiment 40. The composition of any one of embodiments 26-39, wherein the chemotherapeutic compound is a mitotic inhibitor.

Embodiment 41. The composition of embodiment 40, wherein the mitotic inhibitor is vincristine, vinblastine, etoposide, teniposide, ixabepilone, nocodazole, epothilone, vinorelbine, camptothecin, irinotecan, topotecan, amsacrine, or lamellarin D.

Embodiment 42. The composition of embodiment 41, wherein the mitotic inhibitor is a taxane.

Embodiment 43. The composition of embodiment 42, wherein the taxane is cabazitaxel, paclitaxel, 10-deacetylbaccatin III, baccatin III, paclitaxel C, 7-epipaclitaxel, or docetaxel.

Embodiment 44. The composition of embodiment 43, wherein the taxane is albumin-bound paclitaxel.

Embodiment 45. The composition of any one of embodiments 37-44, wherein the amount effective to treat or prevent chemotherapy-induced neuropathic pain is about 1-100 mg/kg.

Embodiment 46. The composition of embodiment 45, wherein the amount is about 1-10 mg/kg.

Embodiment 47. A pharmaceutical composition comprising (a) LR-90 or a pharmaceutically acceptable salt or derivative thereof, and (b) a pharmaceutically acceptable organic solvent.

Embodiment 48. The pharmaceutical composition of embodiment 47, wherein the organic solvent comprises one or more of D-α-Tocopherol polyethylene glycol succinate (TPGS), poly-oxyethylene esters of 12-hydroxystearic acid (Solutol), macrogolgycerol hydroxystearate (Kolliphor RH40), Labrafac, or a cyclodextrin.

Embodiment 49. The pharmaceutical composition of embodiment 48, wherein the organic solvent comprises a cyclodextrin.

Embodiment 50. The pharmaceutical composition of embodiment 49, wherein the cyclodextrin is 2-hydroxypropyl-beta-cyclodextrin (HPβCD).

Embodiment 51. The pharmaceutical composition of embodiment 50, wherein the concentration of HPβCD is from about 10% to about 40%.

Embodiment 52. The pharmaceutical composition of embodiment 51, wherein the concentration of HPβCD is about 20%.

Embodiment 53. The pharmaceutical composition of any one of embodiments 47-52, wherein the pH is from about 7 to about 10.

Embodiment 54. The pharmaceutical composition of embodiment 53, wherein the pH is from about 7.5 to about 8.5.

Embodiment 55. The pharmaceutical composition of embodiment 54, wherein the pH is about 8.

Embodiment 56. The pharmaceutical composition of any one of embodiments 47-55, wherein LR-90 is present in a concentration of about 5 to about 15 mg/ml.

Embodiment 57. The pharmaceutical composition of embodiment 56, wherein LR-90 is present in a concentration of about 5 to about 10 mg/ml.

Embodiment 58. A kit comprising (a) a chemotherapeutic compound, and (b) LR-90 or a pharmaceutically acceptable salt or derivative thereof.

Embodiment 59. The kit of embodiment 58, further comprising a pharmaceutically acceptable carrier.

Embodiment 60. The kit of embodiment 59, wherein the pharmaceutically acceptable carrier is an organic solvent.

Embodiment 61. The kit of embodiment 60, wherein the organic solvent is a cyclodextrin.

Embodiment 62. The kit of embodiment 61, wherein the cyclodextrin is 2-hydroxypropyl-beta-cyclodextrin (HPβCD).

Embodiment 63. The kit of embodiment 62, wherein the concentration of HPβCD is from about 10% to about 40%.

Embodiment 64. The kit of embodiment 63, wherein the concentration of HPβCD is about 20%.

Embodiment 65. The kit of any one of embodiments 58-64, wherein the pH is from about 7 to about 10.

Embodiment 66. The kit of embodiment 65, wherein the pH is from about 7.5 to about 8.5.

Embodiment 67. The kit of embodiment 66, wherein the pH is about 8.

Embodiment 68. The kit of any one of embodiment 58-67, wherein LR-90 is present in a concentration of about 5 to about 15 mg/ml.

Embodiment 69. The kit of embodiment 68, wherein LR-90 is present in a concentration of about 5 to about 10 mg/ml.

Embodiment 70. The kit of embodiment 69, wherein LR-90 is present in an amount effective to treat or prevent chemotherapy-induced neuropathic pain in a subject.

Embodiment 71. The kit of any one of embodiment 57-70 wherein the chemotherapeutic compound is a mitotic inhibitor.

Embodiment 72. The kit of embodiment 71, wherein the mitotic inhibitor is vincristine, vinblastine, etoposide, teniposide, ixabepilone, nocodazole, epothilone, vinorelbine, camptothecin, irinotecan, topotecan, amsacrine, or lamellarin D.

Embodiment 73. The kit of embodiment 71, wherein the mitotic inhibitor is a taxane.

Embodiment 74. The kit of embodiment 73, wherein the taxane is cabazitaxel, paclitaxel, 10-deacetylbaccatin III, baccatin III, paclitaxel C, 7-epipaclitaxel, or docetaxel.

Embodiment 75. The kit of embodiment 74, wherein the taxane is albumin-bound paclitaxel.

Embodiment 76. Use of LR-90 or a pharmaceutically acceptable salt or derivative thereof in treating or preventing chemotherapy-induced neuropathic pain in a subject in need thereof.

The invention claimed is:

1. A method of treating chemotherapy-induced neuropathic pain in a subject in need thereof, wherein said method comprises administering to the subject an effective amount of methylene bis[4,4'-(2-chlorophenylureidophenoxyisobutyric acid)] (LR-90) or a pharmaceutically acceptable salt thereof.

2. The method of claim 1, wherein LR-90 is formulated in a pharmaceutically acceptable carrier and the pharmaceutically acceptable carrier comprises an organic solvent.

3. The method of claim 2, wherein the organic solvent comprises one or more of D-α-Tocopherol polyethylene glycol succinate (TPGS), poly-oxyethylene esters of 12-hydroxystearic acid (Solutol), macrogolgycerol hydroxystearate (Kolliphor RH40), Labrafac, or a cyclodextrin.

4. The method of claim 3, wherein the organic solvent comprises a cyclodextrin.

5. The method of claim 4, wherein the cyclodextrin is 2-hydroxypropyl-beta-cyclodextrin (HPβCD).

6. The method of claim 5, wherein the concentration of HP CD is from about 10% to about 40% (w/v).

7. The method of claim 1, wherein the pH of the pharmaceutically acceptable carrier is from about 7 to about 10.

8. The method of claim 1, wherein the subject has cancer and is receiving or has been prescribed treatment with a chemotherapeutic compound.

9. The method of claim 8, wherein the cancer is a solid tumor cancer, prostate cancer, hormone-refractory prostate cancer, ovarian cancer, breast cancer, head and neck cancer, stomach cancer, lung cancer, non-small cell lung cancer, Kaposi sarcoma, cervical cancer, pancreatic cancer, melanoma, esophageal cancer.

10. The method of claim 8, wherein the chemotherapeutic compound is a mitotic inhibitor, and the mitotic inhibitor is vincristine, vinblastine, etoposide, teniposide, ixabepilone, nocodazole, epothilone, vinorelbine, camptothecin, irinotecan, topotecan, amsacrine, lamellarin D, or taxane.

11. The method of claim 10, wherein the taxane is cabazitaxel, paclitaxel, 10-deacetylbaccatin III, baccatin III, paclitaxel C, 7-epipaclitaxel, docetaxel, or albumin-bound paclitaxel.

12. The method of claim 8, wherein LR-90 is administered before, concurrently with, or after the chemotherapeutic compound, and/or LR-90 is administered orally and the chemotherapeutic compound is administered intravenously.

13. The method of claim 1, wherein the subject is receiving or has been prescribed treatment with cisplatin, dexamethasone, doxorubicin, etoposide, bortezomib, or vinblastine.

14. The method of claim 1, wherein the effective amount is about 1-100 mg/kg.

15. A method of preventing chemotherapy-induced neuropathic pain in a subject in need thereof, wherein said method comprises administering to the subject an effective amount of methylene bis[4,4'-(2-chlorophenylureidophenoxyisobutyric acid)] (LR-90) or a pharmaceutically acceptable salt thereof.

* * * * *